US007930543B2

(12) United States Patent
Corndorf

(10) Patent No.: US 7,930,543 B2
(45) Date of Patent: Apr. 19, 2011

(54) SECURE TELEMETRIC LINK

(75) Inventor: Eric D. Corndorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 909 days.

(21) Appl. No.: 11/828,867

(22) Filed: Jul. 26, 2007

(65) Prior Publication Data

US 2008/0046039 A1 Feb. 21, 2008

Related U.S. Application Data

(60) Provisional application No. 60/838,718, filed on Aug. 18, 2006.

(51) Int. Cl.
*H04L 9/32* (2006.01)
*H04L 29/06* (2006.01)

(52) U.S. Cl. .......................... 713/172; 713/150; 713/164

(58) Field of Classification Search .................. 713/172, 713/164, 150
See application file for complete search history.

(56) References Cited

U.S. PATENT DOCUMENTS

| 4,676,248 | A | 6/1987 | Bernston |
| 5,350,407 | A | 9/1994 | McClure et al. |
| 5,350,411 | A | 9/1994 | Ryan et al. |
| 6,039,251 | A | 3/2000 | Holowko et al. |
| 6,622,050 | B2 | 9/2003 | Thompson |
| 2003/0114897 | A1 | 6/2003 | Von Arx et al. |
| 2004/0246128 | A1 | 12/2004 | Menard |
| 2005/0102167 | A1 | 5/2005 | Kapoor |
| 2005/0203582 | A1 | 9/2005 | Healy et al. |
| 2005/0204134 | A1 | 9/2005 | Von Arx et al. |
| 2005/0283198 | A1 | 12/2005 | Haubrich et al. |
| 2006/0291657 | A1 | 12/2006 | Benson et al. |

OTHER PUBLICATIONS

Perrig (Adrian Perrig, Robert Szewczyk, Victor Wen, David Culler, and Doug Tygar: "SPINS: Security Protocols for Sensor Networks." In Proceedings of the Seventh Annual International Conference on Mobile Computing and Networks (MOBICOM 2001), Jul. 2001.).*
Regatta: A framework for automated supervision of network clouds; Sethaput, V.; Onart, A.; Travostino, F.; Open Architectures and Network Programming Proceedings, 2001 IEEE; Publication Year: 2001, pp. 104-114.*
Research and implementation of a scalable secure active network node; Jian-Guo Wang; Zeng-Zhi Li; Ya-Nan Kou; Machine Learning and Cybernetics, 2002. Proceedings. 2002 International Conference on vol. 1; Publication Year: 2002 , pp. 111-115 vol. 1.*
Threshold Cryptography & Genetic Algorithm Based Secure Key Exchange for Mobile Hosts; Sahoo, D.; Rai, S.C.; Pradhan, S.; Advance Computing Conference, 2009. IACC 2009. IEEE International; Publication Year: 2009 , pp. 1297-1302.*
IEEE Computer Society: 802.15.4 IEEE Standard for Information Technology, Part 15.4b: Wireless Medium Access Control (MAC and Physical Layer (PHY) Specifications for Low-Rate Wireless Personal Area Networks (WPANs) IEEE Standard, Apr. 2006, 194-212-227-246 (XP002462079).

(Continued)

*Primary Examiner* — David Y Jung
(74) *Attorney, Agent, or Firm* — Michael J. Ostrom; Stephen W. Bauer

(57) ABSTRACT

A communications protocol is used to provide data privacy, message integrity, message freshness, and user authentication to telemetric traffic, such as to and from implantable medical devices in a body area network. In certain embodiments, encryption, message integrity, and message freshness are provided through use of token-like nonces and ephemeral session-keys derived from device identification numbers and pseudorandom numbers.

29 Claims, 14 Drawing Sheets

OTHER PUBLICATIONS

U.S. Appl. No. 11/828,940, filed Jul. 26, 2007, by Eric Corndorf.
U.S. Appl. No. 11/828,886, filed Jul. 26, 2007, by Eric Corndorf.
U.S. Appl. No. 11/828,898, filed Jul. 26, 2007, by Eric Corndorft.
Office Action for U.S. Appl. No. 11/828,940, mail date Aug. 23, 2010, 8 pp.
Office Action for U.S. Appl. No. 11/828,886, mail date Aug. 23, 2010, (13 pp.).
International Search Report from corresponding PCT/US2007/075537, Mar. 3, 2008, (6 pp.).
International Preliminary Report on Patentability from corresponding PCT/US2007/075537, dated Feb. 24, 2009,(9 pp.).
Written Opinion from corresponding PCT/US2007/075537, mail date Mar. 3, 2008 (8 pp.).
U.S. Appl. No. 12/341,516, filed Dec. 22, 2008, by Eric Corndorf.
Office Action Response for U.S. Appl. No. 11/828,940, filed Dec. 23, 2010 (15 pp.).
Office Action Response for U.S. Appl. No. 11/828,886, filed Dec. 23, 2010 (15 pp.).

\* cited by examiner

SECURE TELEMETRIC LINK

CROSS REFERENCE TO RELATED APPLICATIONS

This application claims the benefit of U.S. Provisional Application No. 60/838,718, filed Aug. 18, 2006, which is hereby incorporated by reference.

FIELD

The present invention relates to providing secure communications in a data communications setting, particularly in providing security in telemetry between implantable medical devices and external device administration hardware, security in telemetry between implantable medical devices and other implantable medical devices, and security in telemetry between external medical devices and other external medical devices.

BACKGROUND

Improvements in technology relating to implantable medical devices ("IMDs"), especially in the areas of power storage, conservation, and miniaturization, have made it possible to equip modern implantable medical devices with wireless telecommunications functions. The benefits of such communication include the capability to make requests to the IMD to transmit information, for example, remaining battery life, number of therapeutic events that have occurred, or certain patient health data, as well as transmitting instructions to the device to change treatment modalities, frequency, or the like. All of these communications are motivated by the imperative on the part of all parties to maximize the patient's health and treatment outcome, and as part of this criteria for success, are also driven by the desire to avoid a situation where the IMD must be removed from the patient or any invasive procedure relating to the patient becomes necessary. Attendant to the risk involved in any surgical or invasive procedure is the cost associated with such procedures when carried out according to the applicable standard of care.

In utilizing the benefits of communication with an IMD while leaving the IMD in the patient, wireless communications are ideally suited and to date are the only practical way to regularly exchange information with the IMD while it remains in its implanted state. Accordingly, the use of telecommunications for IMD administration may include communications to or from an IMD, or alternatively among in vitro (i.e., not implanted) IMD-administration devices (collectively referred to alternately herein as "telemetry," regardless of whether communications are being transmitted to or from the IMD or administration device, and further regardless of whether a measurement is being transmitted (as opposed to, for example, updated instructions to an IMD).

While telemetry, and particularly IMD telemetry, may make the treatment of disease states or other medical conditions more convenient and effective, it is important to ensure that the use of telemetry does not permit a third-party to interfere in the administration of such devices. For example, eavesdropping alone may compromise patient data that may be protected under certain data privacy regimes, e.g. the Health Insurance Privacy and Accountability Act ("HIPPA"). Even more critically, if a telemetry communication from an administration device to a medical device is interfered with, an important therapy that was intended may not be administered to a patient hosting the implanted device, presumably resulting in suboptimal treatment outcomes. If a malicious third party intercepted a communication and replaced it with a bogus instruction to a device, or even repeated a legitimate instruction to cause an implant to administer incorrect or excessive therapies, adverse effects on the implant's host may result.

To date, most common wireless communications protocols suitable to IMD telemetry applications are of a "broadcast," rather than of a directional nature. Accordingly, if an IMD is in range of a telemetry signal (or, when communications originate with the IMD, a receiving device is in range of the IMD), we may generally assume that any receiving device in range of the signal may access the signal, whether or not that access is intended by the caregiver and/or patient.

The low distance range of many telemetry transactions involving IMDs, has to a certain extent effected a kind of physical layer authentication. In other words, most unauthorized access to IMD-related communications is not feasible because an unauthorized party must be so close to the transmitting device that the physical presence of the eavesdropper (or their tools) would be apparent to the parties legitimately sending or receiving such information. However, the range of telemetry applications is constantly expanding, and at some point it may be contemplated, for example, to interrogate an IMD while a patient is seated in a physician waiting room, even though the intended receiving device is in another room altogether. As the distance necessary for communication between the IMD and external hardware becomes longer, so to does the opportunity for interlopers or eavesdroppers to receive, interfere with, or even manipulate the communications signals.

It is also important that messages are "fresh," i.e., that they have been transmitted recently, and only once. For example, duplicate communications of data from a diagnostic sensor that falsely indicate no change in a patient's physiological condition in spite of therapy being applied may result in excess therapy or other unnecessary medical intervention with its attendant risks. In addition to message privacy (i.e., encryption), true data security requires both message integrity and message freshness. Without all three, gaps will exist that may be exploited by a malicious third party, or indeed may permit errors without malice. Of course, whether or not such exploitation is likely is not particularly relevant from a design standpoint—the security of the telemetry should be ensured to prevent any eavesdropping or interception regardless of the actual potential for problems arising from the interception scenario being considered.

Previous approaches to telemetry security involved, for example, server-based authentication and storage—in this way, no permanent key information would ever be stored on equipment. However, this approach requires a secure communications channel to a server that is available around the clock. It also requires clinicians to be authenticated to the server system prior to their administration of a body area network (BAN) device or node.

Alternatively, biometric tokens (such as key fobs), have been used to authenticate IMD support appliances to IMDs. However, this approach subjected the authentication keys (both the biometric key and the IMD key) to loss, and the token could also be forgotten by patients presenting for IMD administration, which would tend to inconveniently require that care be postponed. Tokens augmented by passwords similarly were subject to loss, noncompliance (failure to bring the token to an appointment, or forgetting the authentication information), and similarly were subject to compromise if lost or stolen.

SUMMARY

The present invention provides a secure system of telemetry communication, particularly well suited to IMD and other medical device administration. A system of protecting the communications to and from IMDs, as well as to and from external devices, is provided. This system implements a system of encryption, in conjunction with an authentication method or methods, in order to ensure that communications to and from communication nodes, and particularly to an from an IMD, are legitimate. In certain embodiments, the legitimacy is ensured, for example, by a rigorous approach to data encryption and key management, and preferably, authentication is secured using at least one modality in addition to the holding of an authenticating card or token.

In certain embodiments, the invention provides for a proximity-dependant "backdoor" that may allow access to and administration of any IMD without the authentication information typically required to permit communications among the nodes or modules within a particular patient's network of medical devices, to be called a "body-area network" or "BAN". The present invention also provides for strong authentication in some embodiments, i.e., zero-knowledge proof of identity, in that authentication is effected without actually transmitting the authentication information (which may of course, subject the authentication information to being compromised).

An unauthorized third party with interests or motives contrary to the patient and authorized caregivers is termed generally herein as an "attacker," regardless of an eavesdropper's identity, location, or motivation. An attacker may wish to simply eavesdrop without actually disrupting communications, perhaps to obtain protected health information regarding the patient, or to learn aspects of the behavior of the BAN nodes proprietary to the BAN node manufacturer. For these purposes, embodiments of the instant invention provide for message privacy (i.e., encryption) through the use of a cipher.

It may also be contemplated that an attacker having sufficient telecommunications and computing power may be able to intercept and control all communications among nodes of a BAN, either eliminating, modifying, duplicating, or otherwise changing messages between nodes. Embodiments of the instant invention provide for message integrity (i.e., message authentication) through the use of message authentication protocols to ensure that instructions to an IMD, for example, and information provided to diagnostic nodes by an IMD are legitimate. Similarly, message freshness may be ensured through freshly-generated session keys and a token-based system, or in alternate embodiments of the instant invention, through the use of time-stamps. The instant invention, in certain embodiments, provides that messages are kept secure from those who do not have the secret key, based on the subsidiary imperatives of message integrity (transmitted messages are received by their intended recipients in an unaltered state) and message freshness (messages are received in a timely fashion, and are not copies of previously transmitted messages, transmitted by an attacker).

Notwithstanding the protections afforded by embodiments of the present invention, the protection of communications is preferably motivated by, and where necessary is subsidiary to, the overall principle of optimal patient care. Accordingly, certain embodiments of the present invention may, in certain emergency or other compelling situations, permit communication with the device by means of a "backdoor" to the device circumventing certain security features of the implementation, in order to prevent adverse health effects, regardless of whether the emergency caregiver has the time or credentials to authenticate him or herself to the device.

Security mechanisms and protocols according to embodiments of the present invention, require that security services have been set up and enabled (rather than bypassed) with respect to at least one of the communicating devices, and may further require the use of an implementation of a block cipher. In other embodiments, all communicating devices of a BAN implementing the invention share an identical body-area network key, $K_{BAN}$, and cooperatively generate a new session key $K_{ses}$, at the start of each new telemetry session. Initially, such device identification exchanges take place via an unsecured exchange, required in order to open a communications session. Packet length for both incoming and outgoing packets are preferably fixed for the duration of a session, and packets not meeting the specified length are preferably rejected in the physical layer of the network.

DETAILED DESCRIPTION OF THE ILLUSTRATED EMBODIMENTS

Figure 1:
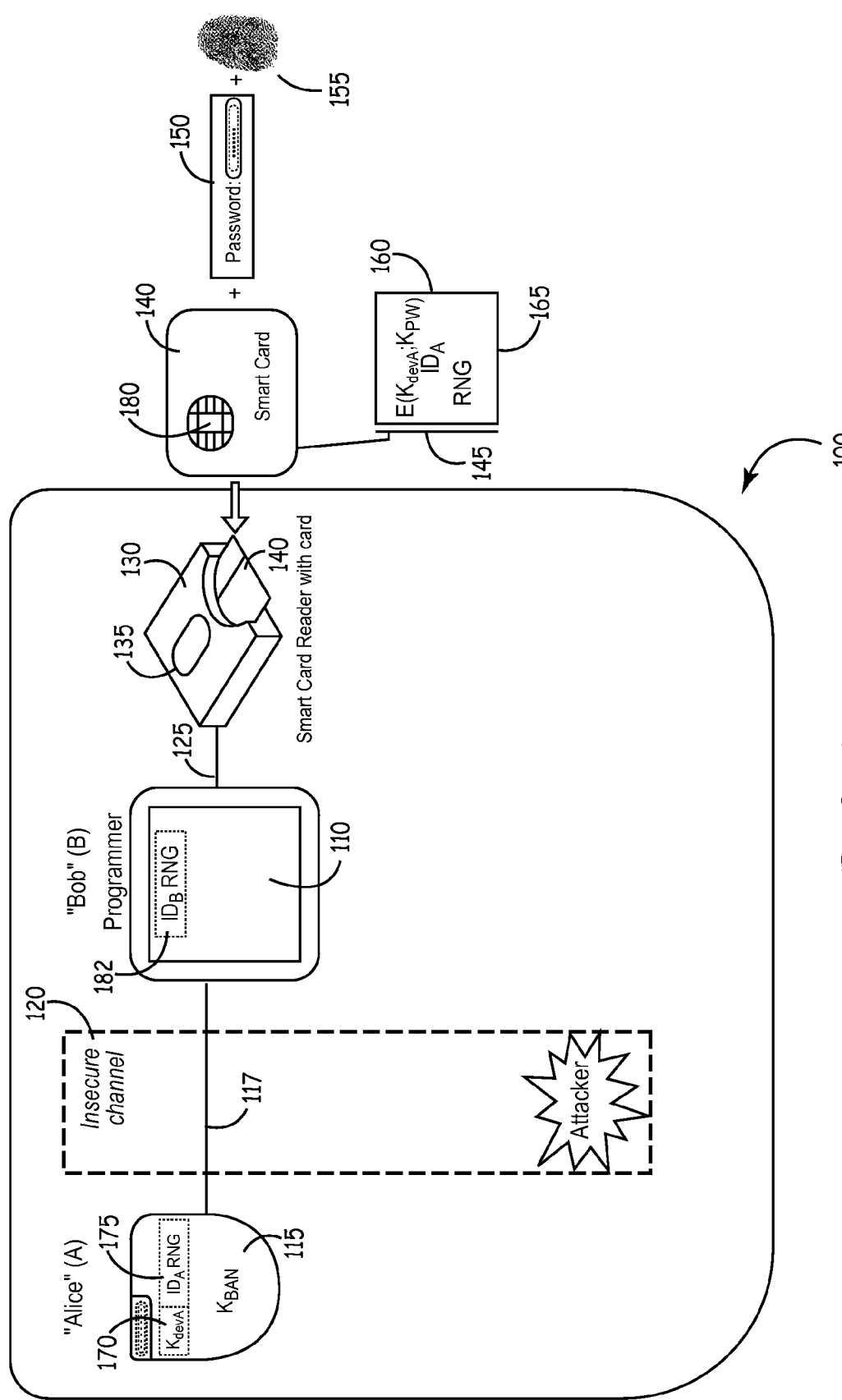
FIG. 1 depicts the general network topography of a body area network according to embodiments of the present invention.

Embodiments of a security implementation for wireless networks according to the present invention may implement a variety of tiers of security or degrees of multi-factor authentication. The tiers of security contemplated herein may be implemented, for example, by a smartcard i.e. a small plastic card or fob typically having an input/output facility (e.g. a port), one or more central processing units, (such as chips), and a number of memory locations. Smartcard technology may be used to implement security by acting as "something the user has" level of security, either by itself or as a component of multi-factor authentication, e.g., coupled with "something the user knows," (i.e. a password) or "something the user is," (i.e. biometric parameters associated with the user).

The cards as implemented according to the present invention will preferably have memory, at least one processor, and data processing capabilities, of the type sometimes referred to as "processor cards" or "microprocessor multifunction cards." The cards may preferably be of the type specified in the International Standards Organization standard ISO 7816 for Integrated Circuit Cards with Electrical Contact, and this assumption is made with respect to the representative embodiments herein. In certain embodiments, certain patient authentication is administered via a smartcard device, however, the IMD's device key is preferably not stored on the smartcard in an unencrypted fashion.

Some embodiments of the present invention provide for the confirmation of what is known herein as the timeliness, or "freshness" of a telemetry communication. For example, a therapeutic modality that may be legitimately directed once, must not be repeatable by a malicious third-party—if a third party can eavesdrop on a communication, based on mere encryption alone, the third party may repeat the instructions repeatedly. Even though the malicious third party doesn't know the content of the message to the IMD, they may reasonably expect the repetition of this message to not do any good for the patient. With enough trial and error, dangerous effects may be implemented by the malicious party even with complete ignorance of the message contents. Embodiments of the present invention therefore also effects a system of ensuring message freshness to prevent such attacks. It will be appreciated that herein, the terms "encrypted" and "secured" are not generally synonymous. Encrypted messages are messages for which only privacy (i.e., secrecy) is assured. Secured messages are messages for which privacy, integrity, freshness, and identity are assured. This latter concept incorporates concepts of authentication, both user authentication (the message actually came from the person (or node) that apparently sent it), and message authentication (the message is in the form sent by the sender, and was sent solely at the time intended by the legitimate sender, and at no other times).

Herein, we may refer to the node (i.e., in a medical device context the implanted or external device, sensor, programmer, monitor, or other appliance within a BAN) transmitting or receiving a communication as "Alice," or "Bob," following the convention of cryptography literature. Alice or Bob will refer to devices or nodes, unless a device user or patient is explicitly mentioned, e.g., Alice's patient or "host," that is, the patient that has the Alice device implanted. Also, we use the term smartcard (including the smartcard when inserted into a smartcard reader/writer) in that in certain embodiments, a smartcard may carry out several functions typically associated with a trusted third-party certificate authority, and upon authentication by the card's holder (e.g. by password and biometric authentication of the holder), the card is regarded as a trusted party within the system, and holds the IMD key corresponding to the IMD in the holder of the card. A third party not intended by the authorized administrators or users of a system to be able to send or receive a message (or a device under the control of such person) will generally be referred to as an "attacker." Also consistent with cryptography literature, we use the symbol ⊕ or "XOR" for the bitwise-exclusive-or operation (i.e., bitwise modulo-2 addition), and the symbol | or || for concatenation. Frequently herein certain software processes or hardware components are described as "knowing," "requesting," "expecting," or "sending" certain information, or carrying out certain functions or activities (e.g. "calculating"), in a manner that may appear to suggest that the software or hardware is a sentient agent. It will be appreciated by those skilled in the art that such anthropomorphic references are not intended to indicate or imply that the hardware or software in question has consciousness, motivation; or intelligence (artificial or otherwise), and these expressions generally are used to indicate the software or hardware's automatic behavior as programmed or instructed, whether by humans or other hardware or software processes or components. For example, a software process that is said to "expect" a certain value may refer to a software function having an argument specified to be a certain variable type or value, with non-conforming arguments processed by error-handling code.

FIG. 1 depicts the topography of a body area network according to embodiments of the present invention. An exemplary body area network (BAN) 100 is shown, consisting of programmer "Bob" 110 and IMD "Alice" 115. These two nodes Alice and Bob have already established an insecure telemetry session 117 over insecure channel 120. Programmer 110 is connected for secure communications (e.g. via a wired connection 125) with authentication device 130, here, a smart card reader/writer having biometric input window 135. According to these embodiments, the following information may be used as authentication data, in increasing order of security, based in each case on a smartcard carried by the patient and used in IMD administration, as described more fully herein.

In a typical embodiment of the present invention, at a minimum, the patient (or other authorized administrator, as applicable) of a device will present a smartcard 140 (something the patient has), containing information annotated as $K_{devA}$ (the key for device 115), $ID_A$ (the identification number for device 115). Further security may be provided by using the patient smartcard 140, plus a password $K_{PW}$ 150, also stored on smartcard element 145 (something the patient has, and something the patient knows), annotated herein as $E(K_{devA}; K_{PW})$, i.e., the device key $K_{devA}$ encrypted by password $K_{PW}$ (or "password key"), $ID_A$, where $E(x;y)$ denotes a function of encryption used to secure "x" using the key "y," or stated otherwise, a certain ciphertext=E(plaintext; key). In certain embodiments, authentication of a user is effected by a patient smartcard 140, or non-electronic information card, plus a password $K_{PW}$ 150, plus a biometric scan $K_{bio}$ or "biometric key" 155 (something the patient has, knows and is), annotated herein as $E(E(K_{devA}; K_{PW}); K_{bio})$, $ID_A$.

As depicted in FIG. 1, Alice's patient (not depicted) has been provided with smartcard device 140, containing memory, firmware, local storage, and/or combination element 145. Alice's patient has initialized smartcard 140 with a password 150 and the patient's biometric feature, here, fingerprint 155.

In certain embodiments of the present invention, smartcards 140 or USB/Firewire® key fobs interfacing with an interface replacing smartcard reader 130 or on-board programmer node 110, may be utilized to implement aspects of the security scheme herein. In certain embodiments, such smartcards or key fobs will have certain ciphers and message-authentication codes (MACs) already implemented and on board the smartcard 140 or key fobs, e.g. implemented in the chip hardware, or alternatively, stored in ROM or flash memory, indicated in the abstract as element 145 on the smartcard or key fob.

In setting up or initializing a BAN which includes an IMD and propagating the BAN key according to the protocols described above, initially the patient will provide their IMD's authentication material (e.g., a smartcard 140) to the bridge device 110. This smartcard 140, for example, may be issued together with the IMD 115 (and given to the patient after surgery), or the necessary information may be entered onto the patient's preexisting smartcard device 140. After inserting their smartcard 140 into the bridge device 110 (here via interface device 130), in certain embodiments, the patient will be prompted to enter their personal password $K_{pw}$ 150 into the bridge device 110 (via a GUI residing on-board programmer 110 or via a suitable separate interface, ideally entered from the patient's own personal memory) and further present a biometric key $K_{bio}$, a value derived from the patient's unique biometric identifier, such as a fingerprint 155 or retinal scan. The bridge device 110 passes the personal password $K_{pw}$ 150 and biometric key $K_{bio}$ 155 onto the smartcard 140 via the smartcard reader 130, preferably without storing $K_{pw}$ 150 and/or $K_{bio}$ 155 in the interim. Using $K_{pw}$ 150 and $K_{bio}$ 155, the smartcard 140 is able to decrypt $K_{devA}$ 170 (i.e., the smartcard may determine $K_{devA}$ 170 using $K_{pw}$ 150 and $K_{bio}$ 155). In certain embodiments, the unencrypted $K_{devA}$ 170 may reside initially in the smartcard's 140 RAM or other memory or storage element 145 until authentication is complete, whereupon preferably it is then deleted and replaced with an encrypted form of $K_{devA}$ 170. Alternatively, non-electronic authentication material in the place of smartcard 140 could be provided to a bridge device 110 in the form of a non-electronic card with the IMD's $K_{devA}$ printed in text or in barcode form, with the BAN propagated according to the protocol of FIG. 3.

The key-delivery protocol of this embodiment of the instant invention provides secure wireless delivery of the current BAN key from IMDs to bridge devices and from bridge devices to IMDs, all within a patient's BAN. The protocol further effects authentication and verification of the sender and receiver, as well as the BAN key itself. Moreover, the invention prevents an attacker from co-opting a device into the attacker's BAN, impersonating a device during delivery of the BAN key, eavesdropping on the delivery process itself, or staging a replay attack based on duplicating earlier communications, because of the requirement that smartcard 140 be available for the communications. Preferably, the $K_{devA}$ key remains securely on the smartcard 140, not on the bridge device 110. Accordingly, even if the bridge device 110 were stolen by an attacker, the attacker would never learn the device key $K_{devA}$. Device keys, generally denoted as $K_{devX}$ herein (such as $K_{devA}$ 170) will preferably be factory programmed with respect to implant devices such as Alice 115, and may be factory-programmed with respect to bridge 110, smart-local, and dumb-local devices as well. These latter devices may also have an externally-labeled $K_{dev}$, or have a random-number $K_{dev}$ that is generated and assigned as needed. Because of the limitations of dumb local devices (particularly in that they have no human interface), such devices will preferably have a factory assigned and externally labeled $K_{devX}$. Alternatively, any of the factory assigned or factory programmed implementations described herein may instead have a $K_{devX}$ or similar information supplied attendant to an updating of flash memory via typical "firmware upgrade" procedures. Herein, the following abbreviations are used to designate different key values and other variables. $K_{devX}$ is the secret device-key for the designated node named X. $K_{BAN}$ is the current BAN session key. $ID_X$ is a device ID, where X is the designated node name.

A suitable security scheme for implementing various privacy and message integrity functions in a representative embodiment of the present invention is the Advanced Encryption Standard ("AES"), similar to Rinjdael, but having a fixed block and key size, and being a standard in common use by the U.S. federal government and communications industry. AES may be suitably used in the configuration CTR+CBC-MAC, as described further herein.

The BAN key will in certain key embodiments be communicated securely from in-vivo devices, particularly, implants such as IMD 115 to other in-vitro "bridge" devices 110 in a BAN 100. The BAN key should also be communicated securely from bridge devices 110 in a BAN 100 to implants 115. According to embodiments of the present invention, there is an underlying communications session 120, which may be unsecured, providing communication between two in-vitro devices 110, or between in-vivo device 115 and in-vitro device 110. Secure communications, such security including encryption as well as integrity and freshness confirmation, is provided by means of authentication material held by the implanted device 115. Implant devices 115 deliver the BAN key to bridge devices 110 who possess the appropriate authentication material 160 and processes such as random number generating facility 165. Implanted devices 115 can also receive the BAN key from bridge devices 110 who possess the appropriate authentication material 160 and processes. According to embodiments of the present invention, the following protocols permit secure and wireless delivery of the BAN key to bridge devices capable of using the security protocol of the present invention.

Figure 2:
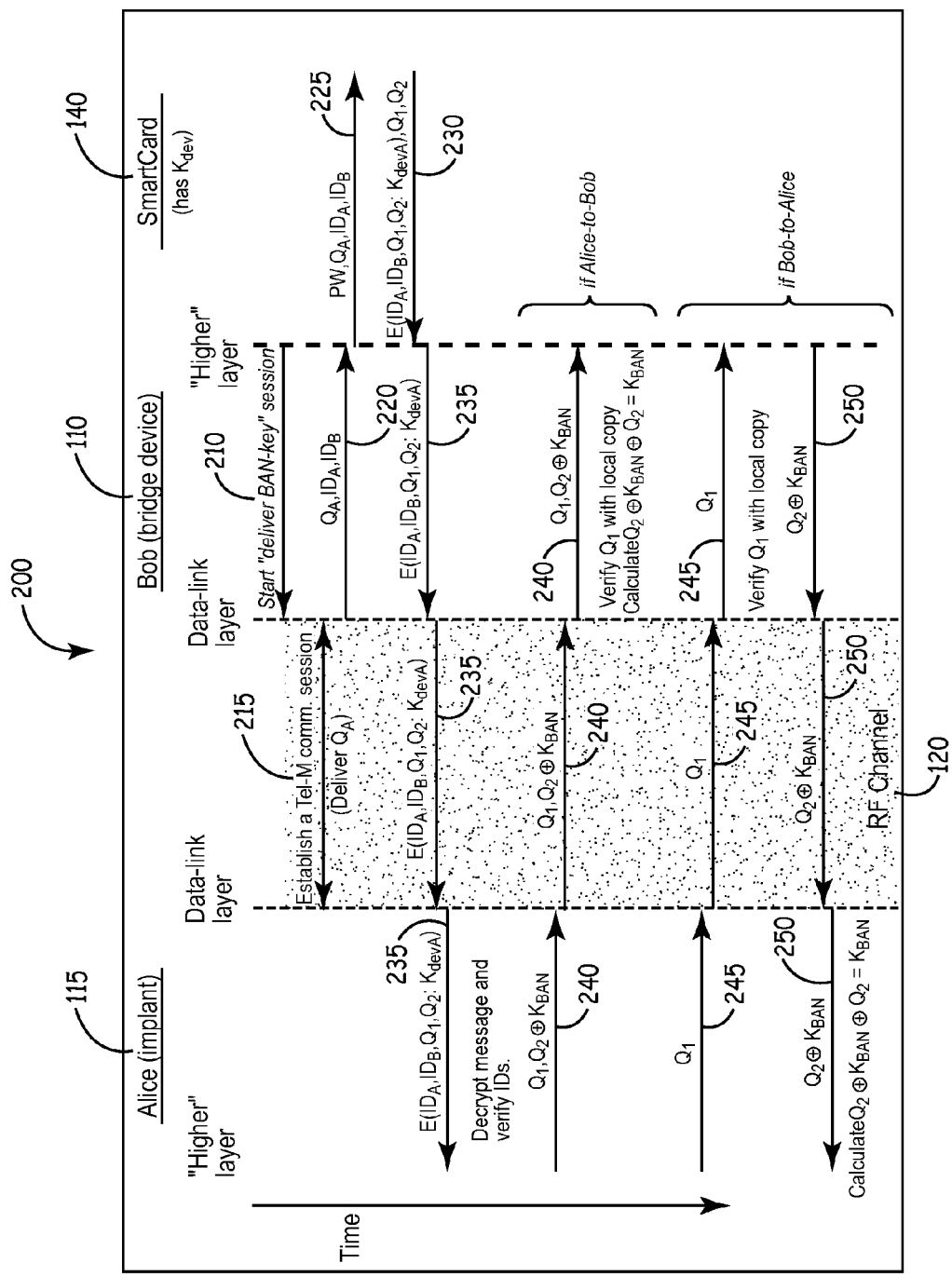
FIG. 2 depicts protocols for the secure transmission of a network key between network nodes according to embodiments of the invention.

FIG. 2 depicts a protocols for the secure transmission of a network key between network nodes according to certain embodiments of the invention. As shown in FIG. 2, implant Alice 115, receives a "deliver BAN-key" session request 210 from bridge device Bob 110, indicating to Alice 115 that Bob 110 wishes to establish or obtain a BAN key. Alice 115 and Bob 110 must initially initiate a telemetric communication session 215 where Alice 115 provides Bob 110 with a freshly-generated random number, $Q_A$. The human administrator of Alice 115 (e.g. the patient having the Alice device 115 implanted) must then present electronic authentication-material (EAM) to Bob 110, e.g. a smartcard 140 through a smartcard reader. This authentication material, typically taking the form of a smartcard 140 or USB/IEEE1394 ("Firewire®") fob, is to contain Alice's device key 170 in FIG. 1, (optionally encrypted), $K_{devA}$ 175, Alice's ID number, $ID_A$, and an onboard microprocessor capable of implementing the block cipher in use (e.g., 128-bit AES). In the event that the copy of $K_{devA}$ 170 residing on the EAM 140 is also encrypted, Alice's human operator should also manually give Bob 110 the secret information needed to decrypt the device key 170, for example, via keypad input (not depicted) such as a PIN or password input, and optional biometric data 155. Once these steps have been completed, Bob 110 prepares and delivers a message 220 to the EAM 140 containing the following: $Q_A$, $ID_A$, $ID_B$, and (as necessary) the secret information 225 (PW 150 and biometric data 155) needed to decrypt the copy of $K_{devA}$ 170 residing on the electronic authentication-material 140. Following the immediate transaction, Bob 110 preferably removes any local record of PW 150 and any biometric information 155. Using its embedded microprocessor 180, the EAM 140 generates two 128-bit random numbers, $Q_1$ and $Q_2$, as described in detail below. The EAM 140 then prepares a block-cipher secured message 230 to Alice 115, using $K_{devA}$ 170 as the key input and $Q_A$ as the nonce, the secured message 230 containing $ID_A$, $ID_B$, $Q_1$, and $Q_2$. as the encrypted payload. The EAM 140 then passes this secured message 230 to Bob 110, along with "unsecured" (i.e., plaintext) copies of $Q_1$ and $Q_2$. Acting as a courier from the EAM 140 to Alice 115, Bob 110 then transmits the EAM's 140 secured message 230 on to Alice as message 235, and temporarily stores the unsecured copies of $Q_1$ and $Q_2$. When Alice 115 receives the EAM's message 230, by way of Bob's telemetry transmission 235, she immediately decrypts the message 235, verifies the accuracy of her ID 175, and then verifies Bob's ID (182 of FIG. 1). If Alice's received message 235 passes its integrity check, Alice 115 is assured that the message 235 is both genuine (from her patient's EAM 140 via Bob 110) and fresh, on account of the fact that the message was secured using $K_{devA}$ 170 and $Q_A$.

If Alice 115 is to deliver the BAN key to Bob 110, then Alice 115 may prepare and transmit an unsecured message 240 to Bob 110 consisting of $Q_1$ and $Q_2 \oplus K_{BAN}$, where $K_{BAN}$ is the current BAN 100 key. On receiving Alice's message 240, Bob 110 verifies that his local $Q_1$ matches Alice's transmitted $Q_1$ (thereby assuring Bob 110 that Alice 115 is the "owner" of the EAM 140, i.e., that the EAM 140 corresponds to Alice's secret device key $K_{devA}$ 170), and XORs his local $Q_2$ with the received $Q_2 \oplus K_{BAN}$ resulting in $K_{BAN}$.

If, on the other hand, Alice 115 is to receive the BAN key from Bob 110, then Alice 115 may prepare and transmit an unsecured message 245 to Bob 110 consisting of $Q_1$. On receiving Alice's message 245, Bob 110 verifies that his local $Q_1$ matches Alice's transmitted $Q_1$ (thereby assuring Bob 110 that Alice 115 is the "owner" of the EAM 140, i.e., that the EAM 140 corresponds to Alice's secret device key $K_{devA}$ 170). Bob 110 may then prepare and transmit an unsecured message 250 to Alice 115 containing $Q_2 \oplus K_{BAN}$. On receiving Bob's message 250, Alice 115 XORs her local $Q_2$ with the received message 250 $Q_2 \oplus K_{BAN}$ resulting in $K_{BAN}$.

Figure 3:
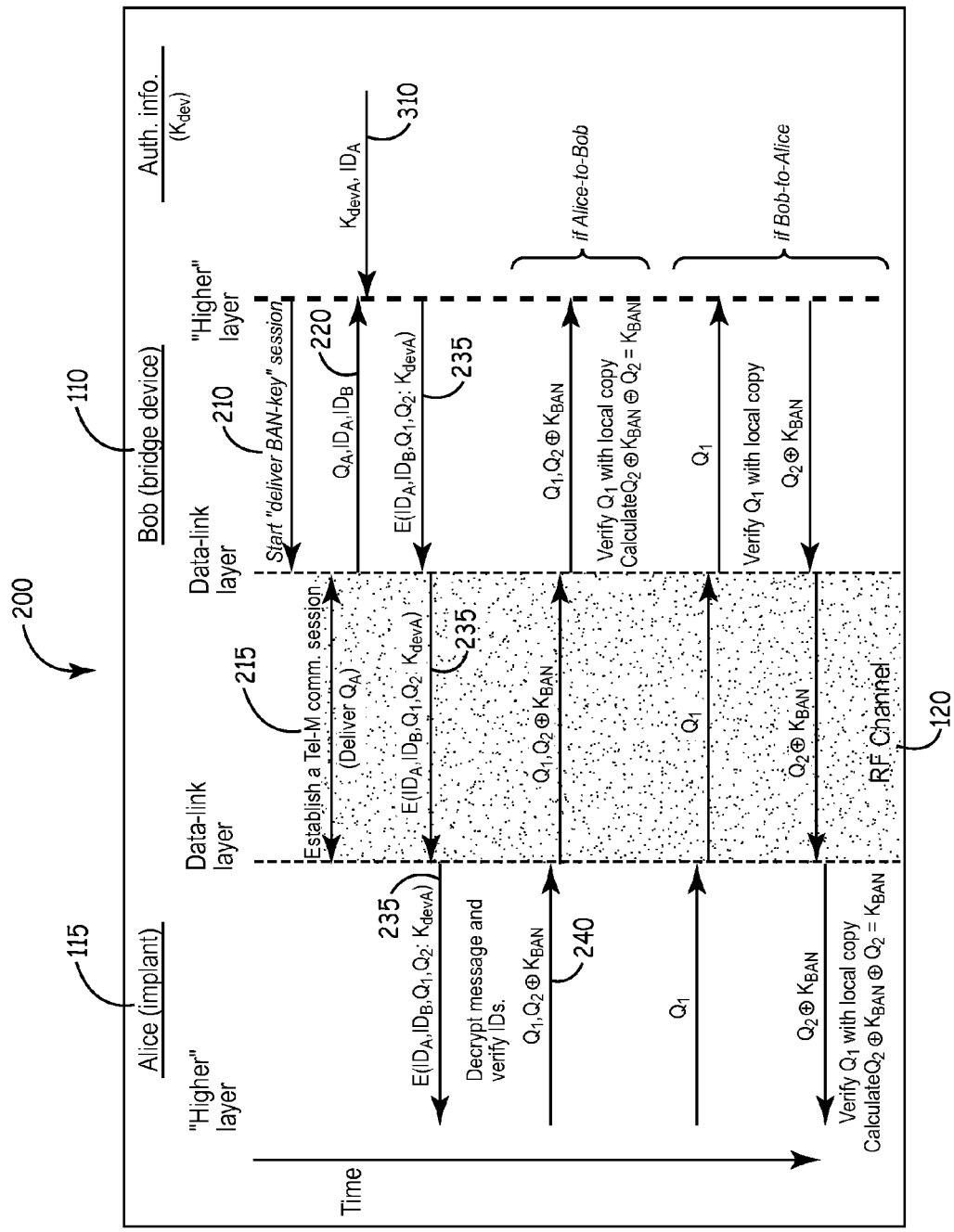
FIG. 3 depicts an alternative embodiment of a network key transmission protocol.

FIG. 3 depicts an alternative embodiment of a body area network key transmission protocol, using authentication items other than the EAM 140 of FIGS. 1 and 2. According to this embodiment, a less secure protocol using less sophisticated non-electronic authentication materials may proceed as follows: According to this embodiment of the protocol 300, Bob 110 may initiate a "deliver BAN key" session request 210 as before Alice, an implant 115, receives a "deliver BAN-key" session request 210 from a bridge device, Bob 110. Alice 115 and Bob 110 must initially initiate a telemetric communication session 215 where Alice 115 provides Bob 110 with a freshly generated random number, $Q_A$. The human administrator of Alice 115 (e.g. the patient having the Alice device implanted) may then present at 310 the non-electronic authentication-material, consisting of $K_{devA}$ 170 and $ID_A$ 175, to Bob 110. This authentication material may, for example, be printed on a identification card in alphanumeric characters or as a barcode, and be read with an optical scanner reader device that may, for example, be internal or integral to Bob, or may alternatively be a separate device in signal communication (e.g. networked) with Bob. Alternatively, the authentication material may be manually inputted by a human administrator directly into bridge device Bob 110 via a GUI or by typing it into a key pad. Using his block cipher (as described herein, or by other means) Bob 110 then generates two 128-bit random numbers, $Q_1$ and $Q_2$, as described above. Bob 110 then prepares a block-cipher secured message 235 to Alice 115, using $K_{devA}$ 170 as the key input and $Q_A$ and the nonce, which contains $ID_A$ 175, $ID_B$ 182, $Q_1$, and $Q_2$. Bob 110 then transmits the secured message 235 on to Alice 115 and temporarily stores the unsecured copies of $Q_1$ and $Q_2$. When Alice 115 receives Bob's message 235, she immediately decrypts the message, verifies the accuracy of her ID 175, and then verifies Bob's ID 182. If Alice's received message 235 passes its integrity check, Alice 115 is assured that the message 235 is both genuine (i.e., is from Bob 110) and fresh on account of the fact that the message 235 was secured using $K_{devA}$ 175 and $Q_A$. Other BAN key generation and transmission occurs as described above.

If Alice 115 is to deliver the BAN key to Bob 110, then Alice 115 may prepare and transmit an unsecured message 240 to Bob 110 consisting of $Q_1$ and $Q_2 \oplus K_{BAN}$, where $K_{BAN}$ is the current BAN 100 key. On receiving Alice's message 240, Bob 110 verifies that his local $Q_1$ matches Alice's transmitted $Q_1$ (thereby assuring Bob 110 that Alice 115 is the "owner" of the EAM 140, i.e., that the EAM 140 corresponds to Alice's secret device key $K_{devA}$ 170), and XORs his local $Q_2$ with the received $Q_2 \oplus K_{BAN}$ resulting in $K_{BAN}$. If, on the other hand, Alice 115 wishes to receive the BAN key from Bob 110, then Alice 115 may prepare and transmit an unsecured message to Bob 110 consisting of $Q_1$. On receiving Alice's message, Bob verifies that his local $Q_1$ matches Alice's transmitted $Q_1$ (thereby assuring Bob 110 that Alice 115 is the "owner" of the EAM 140, i.e., that the EAM 140 corresponds to Alice's secret device key $K_{devA}$ 170). Bob 110 then prepares and transmits an unsecured message to Alice containing $Q_2 \oplus K_{BAN}$. On receiving Bob's message, Alice XORs her local $Q_2$ with the received $Q_2 \oplus K_{BAN}$ resulting in $K_{BAN}$.

Embodiments of the present invention provide for a system by which the manufacturer may place a transceiver module in one of at least four permanent states, depending on the class of device to which the module belongs. These classes may be generally categorized as (1) implant devices (IMDs), (2) bridge devices, (3) smart-local devices, and (4) dumb-local devices. Smart-local devices are those with an extensive graphical user-interface (GUI), including facilities for user input (e.g. external drug pumps, external glucometer controllers, and implant controllers). Bridge devices have extensive GUIs and user inputs, and further are able to authenticate themselves to implant devices (e.g. physician programmers, and the more feature-rich and powerful implant controllers and home monitors). Dumb-local devices are those with no GUI or user input, although there may be some limited user display, and may include key fobs, external glucometers, comlinks, and certain limited capability patient controllers and home monitors.

Regardless of the type of device making up the various nodes of a BAN, in order for these devices to communicate securely with the minimum computing resources necessary, all devices will preferably share the BAN key, $K_{BAN}$. For example, according to the present invention, bridge and/or smart-local devices can deliver a legitimate BAN key to other bridge, smart-local device, dumb-local and implanted devices, on a per-session basis, and specifically the implant device securely delivers the current BAN key to authorized bridge devices of the BAN (e.g., a programmer appliance) or receives the current BAN key from authorized bridge devices (e.g., a programmer appliance). In certain embodiments of the invention, a key delivery protocol is used that prevents or hinders device impersonation during delivery of the BAN key, eavesdropping on BAN key delivery, and/or replay attacks (i.e. the mere repetition of a communication that was eavesdropped upon, including with only a partial understanding or speculation, or even no understanding, of the substantive message contents). Because in-vitro (i.e., outside of body) BAN devices never receive an IMD's secret device key, a device in a patient's BAN, such as a programmer, never learns an IMD's unique device key, which remains secret at all times and is not communicated, the IMD is not compromised even if in vitro equipment used in that IMD's BAN is lost or stolen, as the existing session authentication information will become obsolete, and the IMD's secret key was never stored on the in vitro equipment. The BAN key is preferably securely communicated from in-vitro devices in a BAN (e.g. bridge and smart-local devices) to other in-vitro devices in a BAN (e.g. bridge, smart-local, and dumb-local devices). To effect this, in certain embodiments of the invention, an unsecured telemetry session is established according to the standard handshake, session request, or other pre-established protocol of the underlying wireless communications method. Where administered by a human, the device receiving the BAN key must be able to visually provide the human operating the device delivering the BAN key with the receiving device's device key $K_{dev}$, as well as the receiving device's ID number, in order to permit the human to verify the authentication of the BAN key recipient. The device key $K_{dev}$ in particular will preferably be unique, at least with respect to other devices to be incorporated into a BAN, if not from all other devices the first device may encounter. Also in certain embodiments, smart-local devices and bridge devices will be used for securely delivering the BAN key they may have been provided to other eligible devices in the BAN (all dumb-local devices and/or other smart-local devices and/or other bridge devices). According to a representative embodiment of the present invention, the BAN key will be provided securely over the BAN's wireless connectivity functionality.

Figure 4:
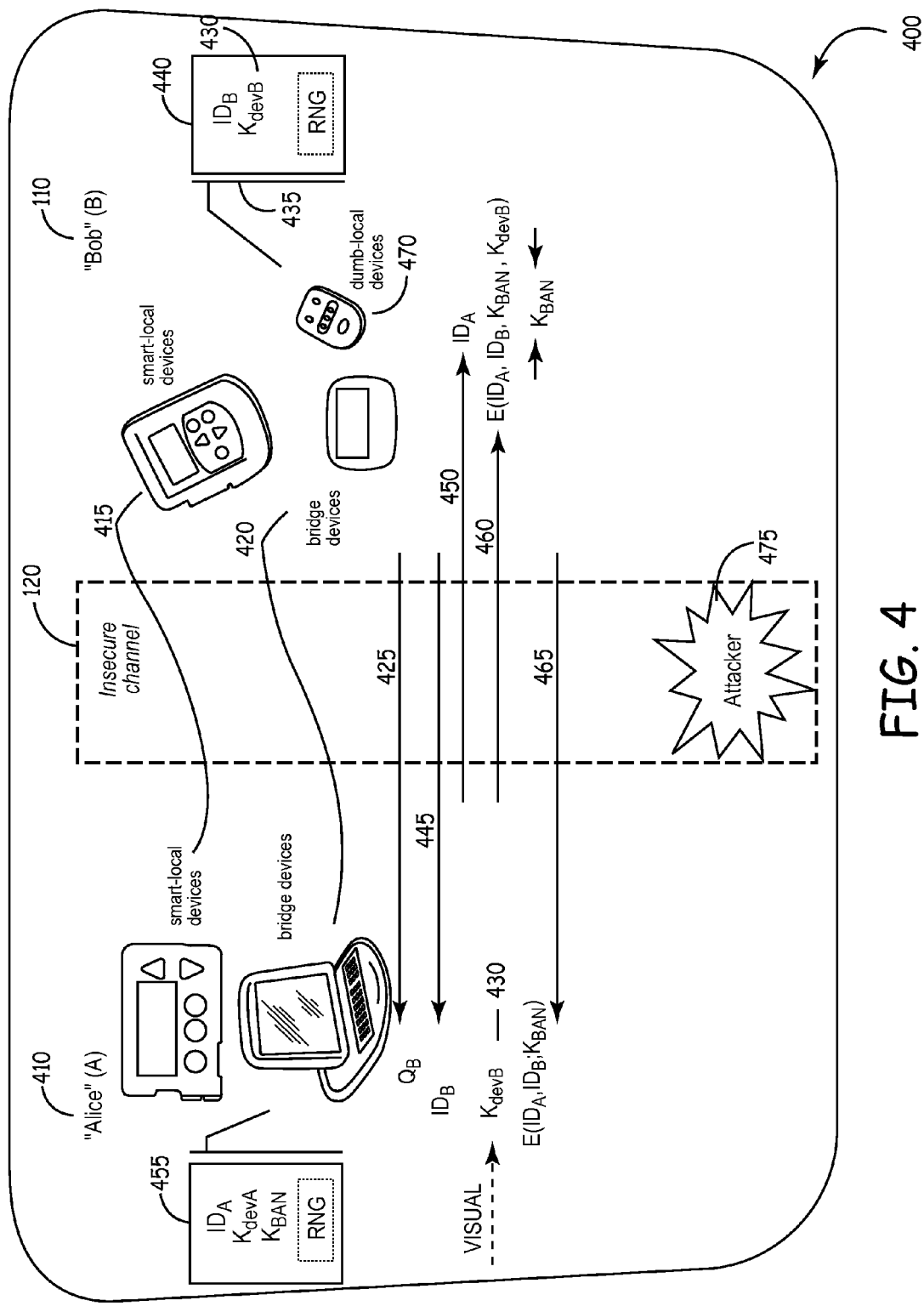
FIG. 4 depicts a topography of a body area network having two in-vitro devices according to an embodiment of the present invention.

FIG. 4 depicts a body area network 400 having two in-vitro devices according to an embodiment of the present invention. A BAN key delivery request may be initiated by the in-vitro device delivering the BAN key (Alice) 410, in this embodiment not an IMD as in previous examples but rather an in-vitro device such as a smart-local device 415 or a bridge device 420. As in earlier BAN key propagation examples, a telemetric communications session is established over an insecure channel 120 (e.g., by handshake or other pre-established compatible session protocol) with the device to receive the BAN key (Bob) 110, and Bob 110 is required to transmit a freshly generated random number, $Q_B$ (generated by RNG facility on-board Bob device 110 memory, storage, or other hardware or software element 435) to Alice 410 via message 425. Once Alice 410 and Bob 110 have otherwise established a telemetry session over insecure channel 120 according to the instant invention, Alice 410 (or the human administering the BAN key exchange session) may visually acquire (and input to Alice 410 via GUI or other input) Bob's device key, $K_{devB}$ 430, which may, for example, be printed on a label affixed to Bob's exterior packaging, or displayed on Bob's electronic GUI and will also be stored in on-board memory or local storage element 435, shown as an abstraction in FIG. 4. Alice and Bob will typically exchange IDs ($ID_A$ and $ID_B$) at the outset of a telemetry session, providing their respective IDs to the other party via communications 445 and 450. In most instances, Alice 410 may also poll or interrogate Bob 110 to obtain Bob's identification number ($ID_B$) 440 via message 445.

Once Alice acquires $ID_B$ 440 and $K_{devB}$ 430, she may access $ID_A$ (Alice's ID number) and the BAN key stored in on-board memory or secure storage 455, and prepare and transmit a message 460 to Bob containing $ID_A$, $ID_B$, and the current BAN key $K_{BAN}$, all secured using Bob's device key $K_{devB}$ 430 as the key input to the block cipher (with $Q_B$ as the nonce input to the block cipher, as detailed below). On receiving Alice's transmission 460, Bob 110 decrypts and verifies Alice's message 460 using $K_{devB}$ 430 and logs the received $ID_A$, $ID_B$, and $K_{BAN}$. Bob then prepares and transmits a message 465 to Alice 410 containing $ID_A$, $ID_B$, all secured with $K_{BAN}$ and $Q_B+1$ (i.e., an incrementation of $Q_B$). On receiving and decrypting/verifying Bob's message 465, Alice 410 verifies that the IDs she received match the IDs she transmitted.

For dumb-local devices 470, the device key $K_{devX}$ may preferably be randomly or arbitrarily chosen "in the factory" and permanently programmed into the device 470 in firmware (or alternatively, flash memory) 435. Because dumb-local devices 470, as defined herein, don't generally have a significant GUI, the $K_{dev}$ 430 will preferably be printed on a label which should be affixed to the external packaging of the device 470, its documentation, or on the device itself, to be removed following initiation. In contrast, smart-local devices 415 and bridge devices 420 as defined herein have a GUI and can thereby make their device keys 430 available by way of an external label (as with dumb-local devices), or through the devices' GUIs. Because $K_{dev}$ is the only piece of information that an attacker would need to know in order to gain access to a telemetry node device from an unauthorized BAN, it is important to keep $K_{dev}$ as private as possible. For smart-local devices 415 and bridge devices 420, it would clearly be more secure if devices keys $K_{dev}$ were only stored in on-board memory/storage 435 or 455, and available solely by way of the devices' GUIs, requiring interaction with the device's GUI, as opposed to being printed on the outside of the device.

While device keys such as $K_{devB}$ 430 are preferably hard-programmed into dumb-local devices 470 (including in flash memory 435), device keys need not be for smart-local devices 415 and bridge devices 420. Accordingly, in certain embodiments of the present invention, device-key privacy for smart-local devices 415 and bridge devices 420 can be maximized if device keys are randomly generated each time that they are needed. Using freshly-generated random numbers for device keys, thereby requiring that the device keys are made viewable by way of a GUI, offers smart-local devices 415 and bridge devices 420 extra immunity from hijacking (i.e., unauthorized use or access) in that the probability distribution of possible device keys is effectively uniform (up to the uniformity of the pseudorandom-number generator) each time that a new device key is generated. This means that an attacker 475 trying to guess a device key 430 would need to start her search over each time that a new device key 430 is generated. Accordingly, in certain embodiments of the invention, freshly-generated random numbers will be used to generate device keys for smart-local devices 415 and bridge devices 420. A block cipher may be used to secure all messages—those messages keyed with the BAN key as well as those keyed with the device key. For example, a block cipher affording strong security without undue overhead may be 128-bit AES. If the device key is shorter that the length of the block cipher, then the device key may be repeated and concatenated to itself as many times as needed in order to reach the length of the block cipher argument.

Figure 5:
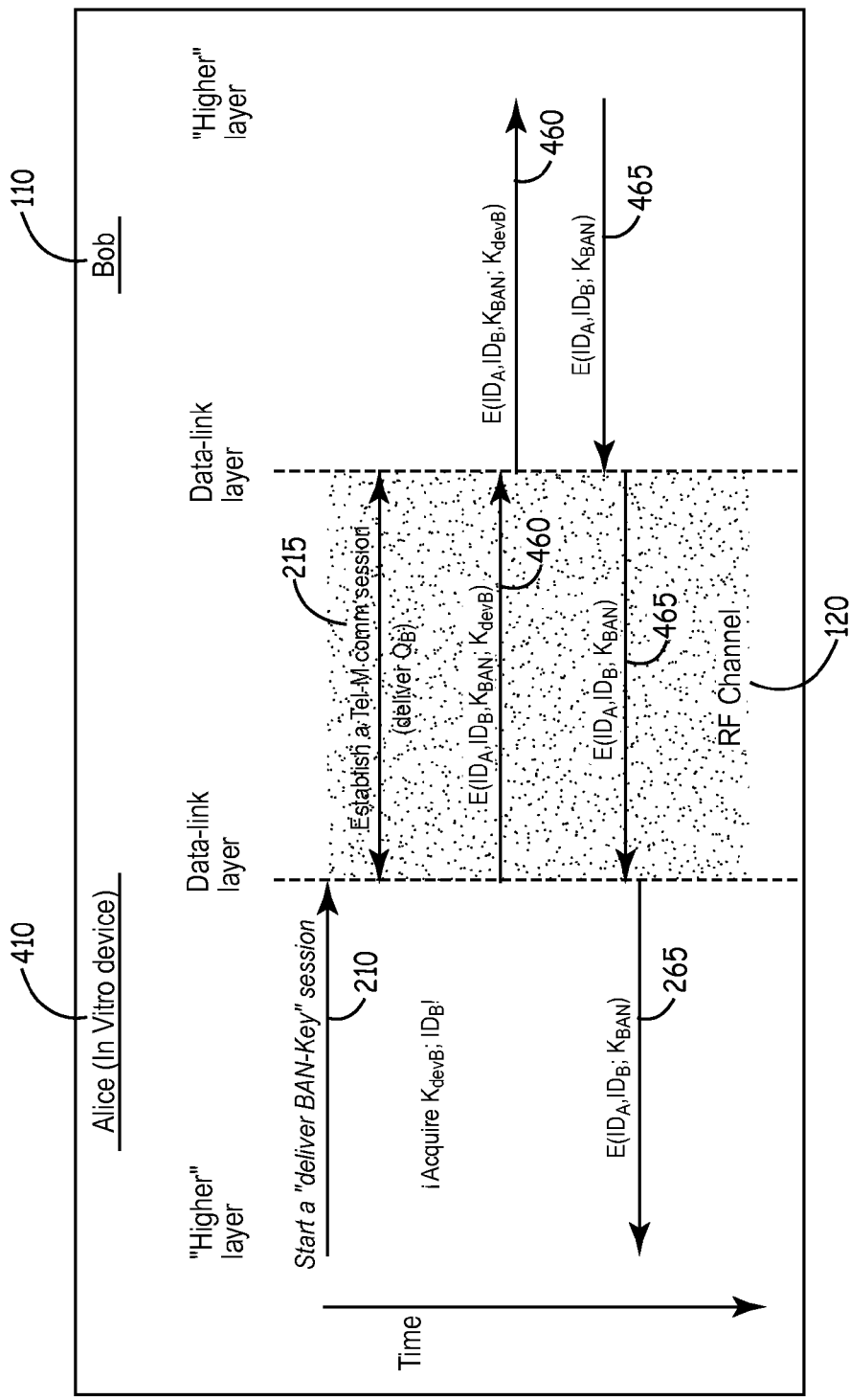
FIG. 5 depicts an alternate embodiment of network key propagation protocol according to the present invention.

FIG. 5 shows the network key propagation protocol of FIG. 4 in pseudo-protocol notation. This protocol describes how the BAN key is to be securely communicated from in-vitro devices in a BAN 400 (bridge devices 420 and smart-local devices 415) to other in-vitro devices in the BAN 400 (either bridge devices 420, smart-local devices 415, and dumb-local devices 470). The device receiving the BAN key, in this case Bob 110, must be able to visually provide the human operating the device delivering the BAN key (in this case Alice 410) an in-vitro device such as a bridge, smart-local, or dumb-local device, with the receiving device's 110 device key $K_{dev}$ 430, as well as the receiving device's ID number 440. Initially, Bob 110 receives a "deliver BAN-key" session request 210 from Alice 410. Alice 410 and Bob 110 must initially initiate a telemetric communication session 215 where Bob 110 provides Alice 410 with a freshly-generated random number, $Q_B$, as with message 425 in FIG. 4. According to certain embodiments of the present invention, smart-local devices 415 and bridge devices 420 are responsible for securely delivering the BAN key, if they have it, to other eligible devices in the BAN 400 (all dumb-local devices 470 and/or other smart-local devices 415 and/or other bridge devices 420). Accordingly, the following protocol is in place to allow for secure and wireless delivery of the BAN key to eligible BAN 400 devices.

As shown in FIG. 5, a "deliver BAN-key" session request 210, which is initiated by the device delivering the BAN key (Alice 410), first consists of establishing an unsecured communications session 215 with the device receiving the BAN key (Bob 110). Once Alice 410 and Bob 110 have established a telemetry session, Bob 110 also needs to send Alice 410 a freshly generated 64-bit pseudo-random number, $Q_B$, via message 215.

An additional and extremely powerful method of preventing device hijacking can be realized if the firmware in smart-local devices 415 and bridge devices 420 refuses incoming "BAN-key delivery" commands 210 unless the human user places the smart-local device 415 or bridge device 420 into an "accept a new BAN-key" mode. The requirement of human intervention in the acceptance of a new BAN-key could be implemented in dumb-local devices 470 with the addition of a dedicated physical button or switch on the dumb-local device 470.

An additional and extremely powerful method of preventing device hijacking can be realized if the firmware 435, 455 in smart-local devices 415 and bridge devices 420 refuses incoming "BAN-key delivery" commands unless a human user in proximity to the device places the smart-local or bridge device into an "accept a new BAN-key" mode. This idea of requiring human intervention in the acceptance of a new BAN-key could also be realized in dumb-local devices 470 with the addition of a physical button or switch (such as a recessed "reset" button) on the dumb-local device 470. While requiring human interaction to accept a new BAN-key practically eliminates any possible device hijacking (provided that that the attacker does not achieve physical contact with the device), other attacks on the BAN-key delivery protocol are possible, as described herein, and are addressed by other embodiments of the invention.

In the last step of the BAN key delivery protocol of FIGS. 4 and 5, Bob 110 may transmit a message 465 to Alice 410, secured with $K_{BAN}$, thus confirming that the key-delivery protocol succeeded. This confirmation signal could be passed up to the application layer and then communicated to the human user as a "delivery successful" notification in the form of a visual and/or acoustic signal.

Bridge devices 420 and smart-local devices 415 of the present invention can in certain embodiments reset BAN keys, thereby also resetting session keys, as described below. For example, at the instruction of a patient or physician, bridge devices 420 and smart-local devices 415 can deliver BAN keys to local devices 415, 470, and/or to other bridge devices 420 by using the receiver's device ID and device key. In certain embodiments of the instant invention, smart local devices 415 can generate BAN keys regardless of whether there are implanted or bridge devices 420 in the BAN. In general, the only time that a BAN key needs to be updated is when a device that has the BAN key is lost or stolen. In certain embodiments according to the present invention, BAN keys would only need to be updated with a frequency on the order of hundreds of years to avoid being compromised, based on current attacker processing power.

Because of networking resource constraints, in certain embodiments of the present invention, a common secret key will be shared by all devices in a particular body-area network (BAN). The BAN key, $K_{BAN}$, will be used to secure all communications within the BAN. Within a BAN, a telemetry session may be established as follows: On the command of any device initiating a telemetry session, the shared BAN key, along with freshly generated and shared random numbers contributed by all BAN members wishing to communicate in the current telemetry session, are distilled into a session key, $K_{ses}$, which is used to secure all messages communicated in the BAN for the duration of the telemetry session. Once the telemetry session is closed, the current session key is discarded.

In order to open a communications session between nodes, initially an unsecured exchange takes place between the communicating devices, e.g., by means of a handshake, session request/accept, or other session initiation protocol. Preferably incoming and outgoing packet lengths are fixed, and moreover, in certain embodiments according to the present invention, the physical-layer hardware is set up to expect these packet lengths—shorter or longer packets may accordingly be flagged and rejected as "bad." An instance of the relevant cipher to be used must be available. One of various suitable encryption standards for use with the present invention is the FIPS-approved 128-bit AES block cipher (FIPS PUB 197). Encryption may be suitably performed in the "counter mode" (CTR mode) of AES. Message freshness may be checked through use of token-like nonces (i.e., single-use pseudorandom numbers). Also in certain embodiments, message integrity will be maintained, for instance by use of the "cipher-block-chaining message-authentication-code mode" (CBC-MAC mode) of AES. In the telemetry security system of the present invention, pseudorandom numbers must be generated from time to time, as discussed herein. We may refer to so-called pseudorandom numbers (as opposed to truly random numbers) to be technically precise when referring to computer-generated numbers, in that the computer-generated numbers are in fact deterministic. However, the pseudorandom numbers are preferably derived from sufficiently complex or varied states or subsidiary functions that the overall function behaves for observable purposes as a stochastic process overall. It will be appreciated that the actual value of the number is immaterial, the number may be used, in certain embodiments, as a seed for a cipher, message authentication function, or even the generation of another pseudorandom number. Because the actual value of the number is immaterial as regards the function of the pseudorandom number, the value of the number may be said to be arbitrary, which herein is intended to be generally synonymous with "aleatory." In general, wherever the present invention calls for the use of pseudorandom number, the functionality may be replaced by, e.g., an alternate pseudorandom number generator, or a hardware-generated random number according to alternate embodiments of the present invention. In certain embodiments, the FIPS-approved AES block cipher specification described above provides for the implementation of a NIST-recommended pseudorandom-number generator (PRNG) based on the ANSI X9.31 specification (appendix A.2.4), which is suitable for typical embodiments of the present invention. This specific embodiment of the ANSI X.9.31 PRNG specification uses the AES block-cipher (FIPS PUB 197). Embodiments of this type generate PRNG pseudorandom numbers 128 bits at a time.

Figure 6:
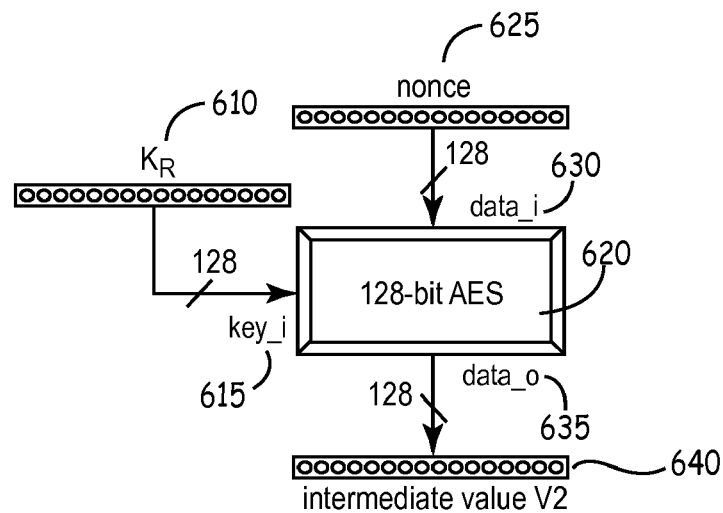
FIGS. 6 through 9 depict data flow diagrams of pseudorandom number generator functions according to certain embodiments of the present invention.

FIGS. 6 through 9 depict data flow diagrams of pseudorandom number generator functions according to certain embodiments of the present invention. FIG. 6 depicts a data flow diagram of the first step of the random number generator of FIG. 9, according to embodiments of the present invention. In certain embodiments, generation of a 128-bit pseudo-random number (PRN) is implemented using the AES block-cipher, as specified in ANSI X9.31, providing adequate security and privacy in light of anticipated attacker processing power, without undue overhead. As an initial matter, 128-bit random numbers $K_R$ 610 and $R_0$ are available to the PRNG. $K_R$ 610, the PRNG key, does not change and is always loaded into the key_i input 615 of the block cipher 620 by way of a 128-bit register. $R_0$ is the PRNG's secret and random initialization-vector which is updated with the new and current PRN ($R_1, R_2, \ldots$) every time the PRNG generates a 128-bit random number. Both $K_R$ 610 and the current R may be stored in memory or secure local storage as they are required for the generation of any new pseudorandom numbers.

In this embodiment, generation of every $(i+1)^{th}$ PRN proceeds as follows: The block cipher 620 (in this example, 128-bit AES) is used to encrypt a nonce 625 using $K_R$ 610 as the key input 615, as depicted in FIG. 6. The nonce 625, which could, for example, consist of the node's current real-time clock value, may be loaded into the 128-bit data_i input 630 of the block cipher 620 by way of a 128-bit register. (If the real-time clock is longer than 128 bits, then the least-significant 128 bits of the real-time clock may be used.) If the real-time clock is shorter than 128 bits, the most-significant bits of the nonce 625 may be padded with zeros such that the number of zeros plus the number of real-time clock bits equals 128. Whether or not the real-time clock is used to generate the nonce 625 the intermediate value data_o 635 outputted from the block cipher 620 may be called $V_1$ 640 herein.

Figure 7:
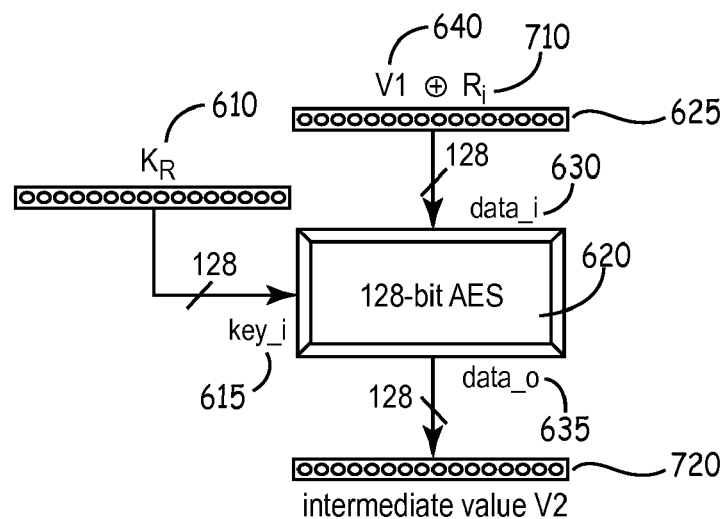

FIG. 7 depicts a step subsequent to that of FIG. 6 in an embodiment of a pseudorandom number generator according to the instant invention. As depicted in FIG. 7, intermediate value $V_1$ 640 is XORed with the current R 710 ($R_0$ for the first random number, or $R_i$ for the $(i+1)^{th}$ random number). This 128-bit value, $V_1 \oplus R_i$, 625 may then be encrypted with the block cipher 620. Specifically, $K_R$ 610 may be loaded into the key_i input 615 of the block cipher 620, for example from a 128-bit register. Following that, $V_1 \oplus R_i$ 625 may be loaded into the data_i input 630 of the block cipher 620 by way of another 128-bit register. Intermediate value $V_2$ 720 is the data_o output 635 of the block cipher 620.

Figure 8:
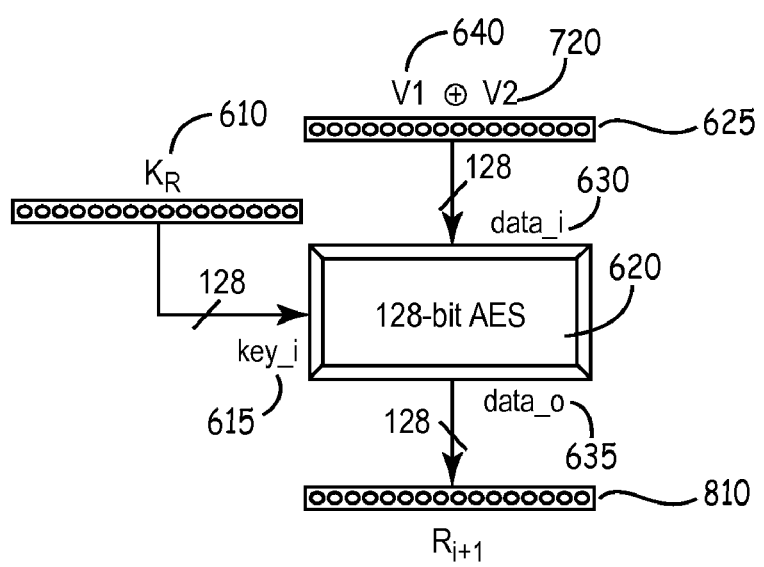

FIG. 8 depicts a step subsequent to that of FIG. 7 in an embodiment of a pseudorandom number generator according to the instant invention. In this embodiment, the 128-bit intermediate values $V_1$ 640 and $V_2$ 720 are XORed together and encrypted with the block cipher 620. Specifically $K_R$ 610 is loaded into the key_i input 615 of the block cipher 620 by way of a 128-bit register. The $V_1 \oplus V_2$ 625 result is loaded into the data_i 630 input of the block cipher 620 by way of another 128-bit register. The output data_o 635 of the block cipher 620 contains the new PRN, $R_{i+1}$ 810. In the event that further 128-bit PRNs are needed, the RNG process may be repeated using a new nonce 625 (the current real-time clock data, for example) and using the newly updated PRN $R_{i+1}$ 810. If no additional random numbers are required, then $R_{i+1}$ is to be stored in memory for the generation of future PRNs in future sessions. The PRNG key, $K_R$ 610, may be stored in memory or secure local storage.

Figure 9:
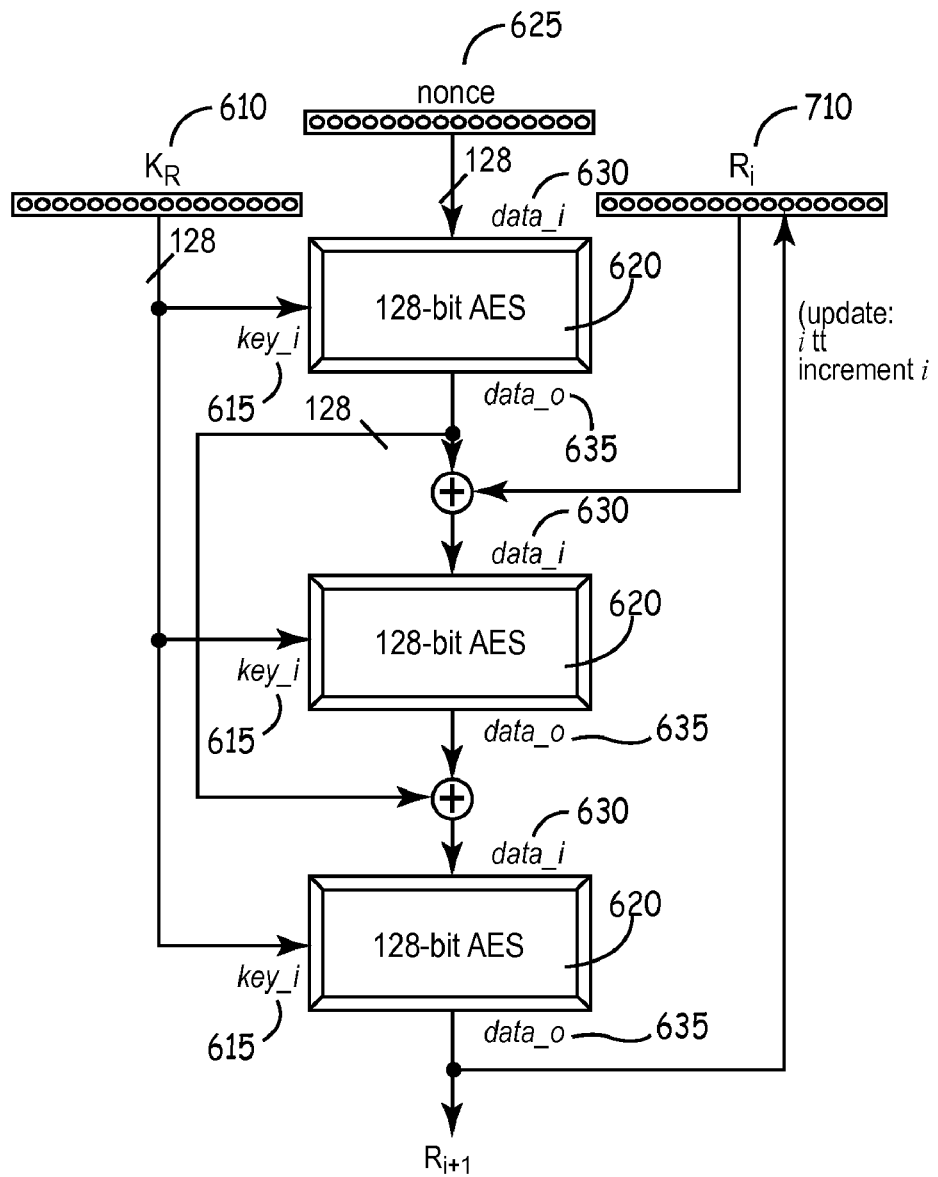

To summarize, the generation of the PRNG key preferably proceeds as follows, as depicted in FIG. 9. If the block cipher is represented by the function E(data_i; key_i)=data_o, where E represents the AES function 620, with the relevant arguments to the function and data_i 630 and key_i 615 (with $i \geq 0$), then the algorithm can be summarized according to 3 steps of nested or iterative processing through the block cipher:

Step 1. $V_1$ 640=E(nonce 625; $K_R$ 610)
Step 2. $V_2$ 720=E($V_1$ 640$\oplus R_i$ 710; $K_R$ 610)
Step 3. $R_{i+1}$ 810=E($V_1$ 640$\oplus V_2$ 720; $K_R$ 610). Combining all three of the above steps gives $R_{i+1}$=E(E(nonce; $K_R$)$\oplus$E($R_i \oplus$E(nonce; $K_R$); $K_R$); $K_R$), In certain embodiments of the instant invention, the PRN generation is allocated use of a 128-bit AES block-cipher 620 and modulo-2 addition functionality, three 128-bit registers to buffer the block-cipher, access to the real-time clock or another nonce 625 source, and storage space for two 128-bit numbers, $R_i$ 710 and $K_R$ 610. Of these, the storage space for $R_i$ and $K_R$, may be unavailable to other aspects and functions of the invention. Preferably, two 128-bit random numbers may be "installed" into a module implementation of the present invention, e.g., in production. One of these random numbers ($K_R$ 610) may be permanent and the other, $R_0$ 710, may preferably be updated every time a new pseudorandom number is generated.

A secure telemetry session according to the present invention is preferably to be initiated whenever one or more communicating devices request a secure session. Setting up a secure communications session is a two-step process, by which all communicating devices are provided the same session key, Kses. In step one, all communicating devices take turns announcing a previously generated pseudo-random number, e.g., a 64-bit random number, called Rx, where "x" indexes the different devices. As described above and depicted in FIGS. 6 through 9, in certain embodiments pseudo-random numbers are generated at the end of the previous secure communications session so that they are immediately available for the next secure session. The generation of these pseudo-random may preferably take place according to the disclosure herein, but other methods of generating pseudo-random numbers or hardware-generated random numbers may be substituted in accordance with the present invention.

Following the announcement of the previously generated random number, the next step provides for the establishment of a secure session, and requires that all communicating devices calculate a common session key (Kses) which will subsequently be used to secure data traffic for the duration of the secure session. Kses is calculated independently but identically by each device using a cipher, such as a block cipher. The 128-bit AES block cipher is suitable for typical embodiments of the present invention.

Figure 10:
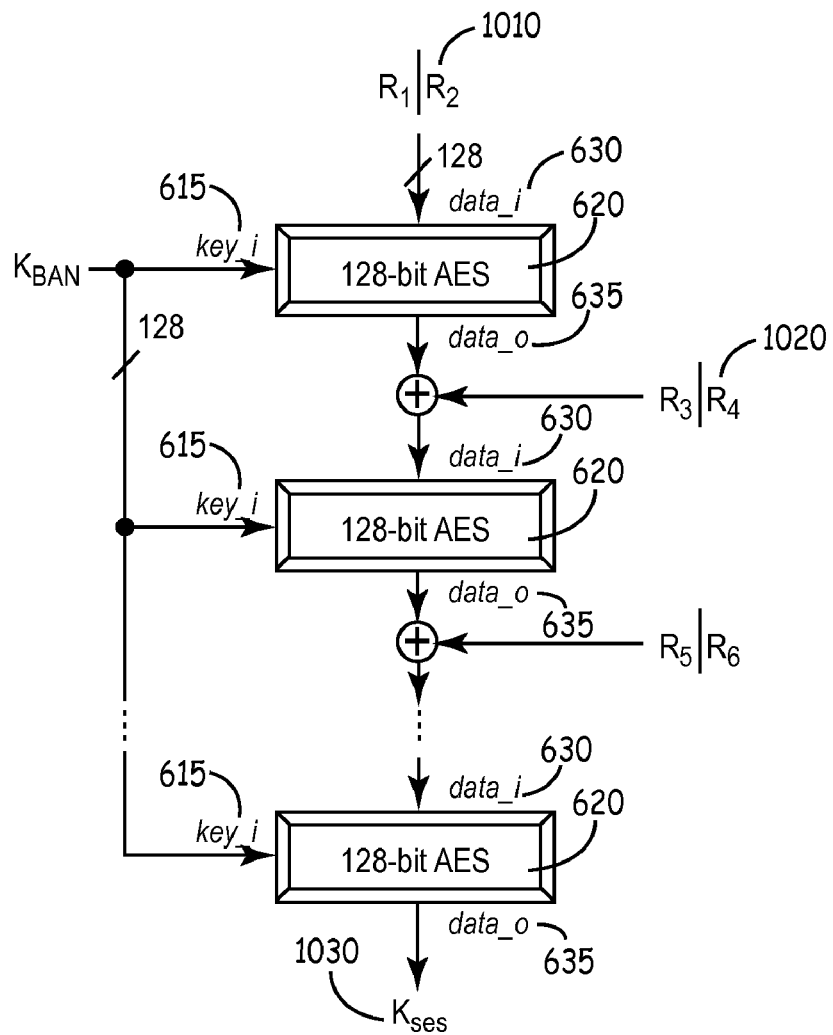
FIG. 10 is a data flow diagram of the generation of a session key according to embodiments of the present invention.

FIG. 10 is a data flow diagram of the generation of a session key according to embodiments of the present invention. The common session key may be derived from the previously-established BAN key, $K_{BAN}$, and all of the communicating nodes random numbers $\{R_1, R_2, R_3 \ldots\}$. In certain embodiments, Kses may be calculated by loading $K_{BAN}$ into the "key input" 615 to the block cipher 620 and loading the devices' random numbers 1010 into the "data in" 630 of the block cipher 620. This may be accomplished by firmware control in certain embodiments of the present invention. Specifically, the first two devices' 64-bit random numbers are to be concatenated to a 128-bit number which is then loaded into the "data in" 630 of the block cipher 620. If there are only two devices wishing to establish a secure session, then the 128-bit output 635 of the block cipher 620 is the session key, Kses. If there are more than two devices wishing to communicate securely within a single session, then the output 635 of the block cipher 620 is then XORed (i.e., modulo-2 added) to the next two devices' 1020 concatenated 128-bit (2×64-bit) random number before again entering the "data in" 630 of the block cipher 620 and getting processed as above. The application of the cipher (here, 128-bit AES) to the XOR-derived value 635 is preferably repeated as many times as is needed to get through all of the devices' random numbers, where the final output 635 of the block cipher 620 is Kses 1030. In the event that there are an odd number of devices to be included in a secure session, an "empty" slot in the 128-bit concatenation may be filled with 64 zeros. At the conclusion of the secure-communications session, the ephemeral Kses 1030 may be "deleted" and a new session key 1030 is calculated at the beginning of each new secure telemetry session, as provided.

Figure 11:
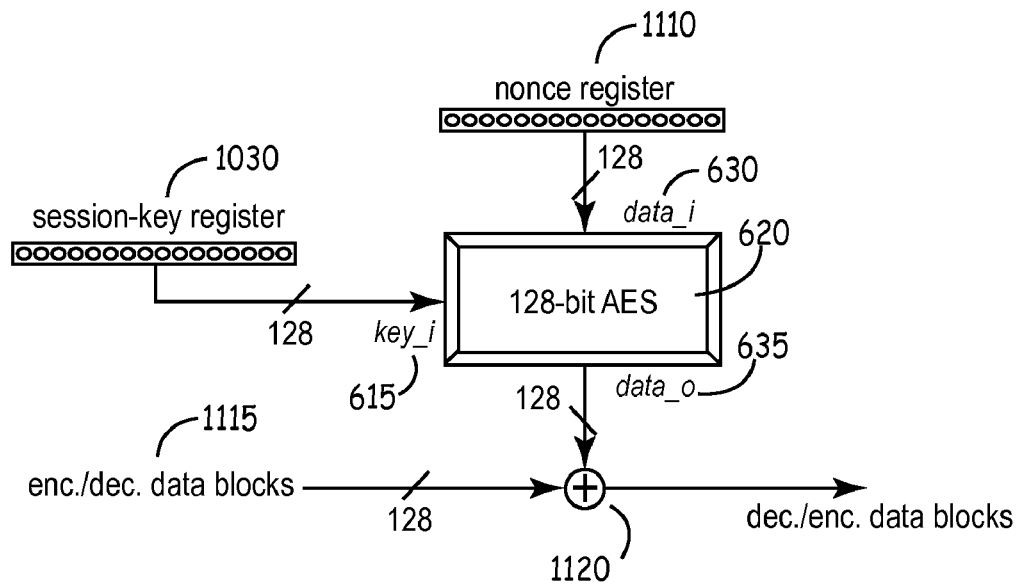
FIG. 11 shows the data flow of the CTR-mode encryption and decryption of a message according to embodiments of the present invention.

As described, the securing of information in certain embodiments may be based on ciphers, including by the use of block ciphers, for example, used in their counter (CTR) mode. In this way, the block cipher may be applied to streams in that the block cipher generates a keyed, pseudo-random keystream which is then XORed against the plaintext in order to generate encrypted text (or, at the recipient node, applied against the ciphertext to generate plaintext to effect decryption). FIG. 11 shows the data flow of the CTR-mode encryption and decryption of a message according to embodiments of the present invention. As depicted, the shared session key 1030 is loaded into the key_i input 615 of the block cipher 620 by way of a 128-bit register; the session key 1030 may be loaded into the register from memory or storage (after being calculated at the initiation of a secure session as discussed above). A 128-bit nonce (i.e., a number used only once) 1110 is loaded into the data_i input 630 of the block cipher 620 by way of another 128-bit register.

Figure 12:
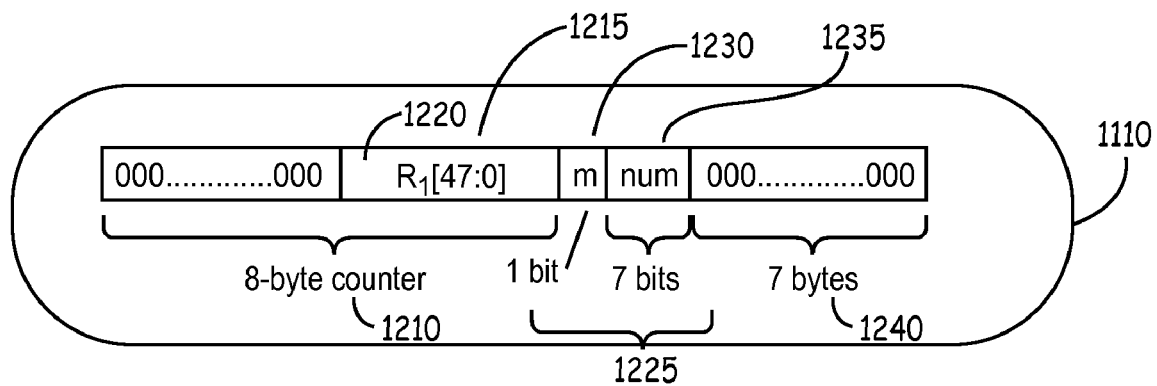
FIG. 12 shows the data structure of a nonce register according to embodiments of the present invention.

FIG. 12 shows the data structure of a nonce register according to embodiments of the present invention. In this embodiment, the most significant eight bytes 1210 of the 128-bit nonce 1110, as shown in FIG. 12, are actually an eight-byte up-counter 1210, while the lower six bytes of that counter 1215 are initiated with the least-significant six bytes [i.e., bits 47 though 0] of the instigating device's random number Rx 1220. It will be appreciated that the random number Rx 1220 was contributed to the generation of the session key 1030 of FIG. 10. Every time that a telemetry packet according to the present invention is received or transmitted in a secure session, the value of the counter 1210 is incremented. The next nonce byte 1225 (just below the eight-byte counter 1220) contains the mode bit 1230, bit "m" 1230 in FIG. 12. This bit may be set to logical zero when the nonce is being used for CTR-mode encryption/decryption; the mode bit is to be set to logical one when the nonce is being used for message integrity, as described herein. The seven-bit field below the mode bit, the block-number field 1240, is to be reset to logical 0000000 at the start of every packet and incremented on the generation of each 128-bit block of keystream material to be used for encryption/decryption within that packet. If, for example, each telemetry packet required 300 bits of keystream material for encryption/decryption, then the first 128 bits of keystream would be generated using 0000000, the second 128 bits would be generated using 0000001, and the third 128 bits would be generated using 0000010 (incrementing by 1, noting that in an example where 300 bits of keystream material are required per packet, only 44 of the last 128 bits of keystream material would be needed). The remaining seven bytes of the 128-bit nonce 1110 (the least-significant seven bytes 1240), may preferably be permanently set to logical zero.

Rather than or in addition to synchronized timestamps to help prevent replay attacks, in certain embodiments of the present invention, message freshness and user authentication is provided by calculating a new session key Kses 1030 at the start of every secure telemetric session, the new session key 1030 being a function of the contribution of random numbers generated by each of the participants in the secure session. With regard to intra-session replay attacks, however, a further freshness mechanism may be provided—in this case, the devices in a secure session should never allow the counter in their local copy of the session nonce to be reset to a value lower than its current value. In the event that a telemetry communications session is interrupted or for some other reason needs to be "reset" or resynchronized within the underlying communications protocol, it might be necessary for the current session nonce to be announced in order for devices in a secure session to resynchronize. An attacker could conceivably attempt to exploit such a situation by trying to reset other session participants' nonces to a previous value, thereby allowing the attacker to replay old messages that used the previous nonce value. In this way, the session nonce acts as something of a network token. If nonce counters only increase, no old message will ever have a legitimate nonce, as past intra-session messages have an earlier nonce, provided that no more than $2^{64}$ packets are communicated in a single secure session, which is unlikely.

As depicted in FIG. 11, in embodiments of the present invention, encryption and decryption are preferably performed by executing a bitwise modulo-2 addition (XOR) between the 128-bit output bus, data_o 635 of the block cipher 620, and 128-bit blocks of data 1115, taken from the payload plaintext for encryption, and from the payload ciphertext for decryption. In certain embodiments of the present invention, packet headers are not encrypted.

Figure 13:
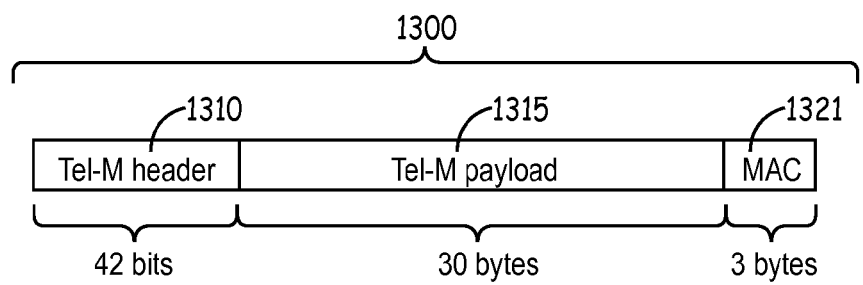
FIG. 13 shows a data structure for a telemetry packet according to an embodiment of the present invention.

FIG. 13 shows a data structure for a telemetry packet 1300 according to an embodiment of the present invention. Each of the 128-bit message blocks 1115 may be XORed 1120 with a different output 635 of the block cipher 620, e.g., message block $m_1$ 1310 of FIG. 13 is to be XORed with keystream block (i.e., the 128-bit block leaving the data_o bus 635 of the block cipher 620) $s_1$, message block $m_2$ (the next 128-bits of packet 1320) is to be XORed with $s_2$, etc. As previously stated, a different nonce 1110 is to be used in the generation of each keystream block 635. In certain embodiments, the same nonce 1110 is never used twice within the same session; accordingly, when the eight-byte nonce counter 1210 reaches its maximum value (0xhFFFFFFFFFFFFFFFF), the secure session may be terminated, with a new session key collectively calculated. In this embodiment, the number of telemetry packets that can be communicated using a single session key is from $2^{64}$ (corresponding to the case where the least-significant six bytes of the instigator's random number is 0xh000000000000) to $2^{64}$-$2^{48}$ (corresponding to the case where the least-significant six bytes of the instigator's random number is 0xhFFFFFFFFFFFF). In base10, these numbers are $1.84467 \times 10^{19}$ and $1.84464 \times 10^{19}$, respectively, thus it will be appreciated that these packet numbers are unlikely to ever be reached in practice.

In a secured network, e.g. a TDMA structure, preferably devices will increment their nonce counters regardless of whether or not the devices actually broadcasts during their allocated window, in order to maintain secure communications during a period of non-transmission, during which time the device may power-down its radio in order to conserve energy. On power up, the device has kept track of the session nonce, and will still be able to power-up later and communicate securely. Alternatively, the "master" or "beacon" of a telemetry network session could broadcast, unsecured, the current nonce counter every time it starts a new "round" within the network session.

In certain embodiments of the present invention, MACs will be calculated on and appended to each telemetry packet. Also in certain embodiments of the invention, one packet size and structure is used. One possible embodiment for such packet structure is depicted in FIG. 13. As shown, a packet 1300 according to the present invention may consist of a 42-bit (5.25 byte) header 1310, a 30-byte payload 1315, and a 3-byte MAC 1320.

In certain embodiments of the invention, a block-cipher (e.g., 128-bit AES) may be used in the CBC-MAC mode to generate a keyed hash-value (the message authentication code, or MAC) of the plaintext of a message, which as depicted in FIG. 13, is to be appended at 1320 to an encrypted form of that message 1315 upon transmission. On reception of these packets 1300 and their appended MACs 1320, the receiver may decrypt the packet payloads 1315, calculate the MAC on their decrypted packets, and compare the calculated MAC value they derived from the received payload 1315, to the MAC value 1320 received as appended to the instant packet 1300. If the MACs match, the packet 1300 is accepted. Naturally if the MACs conflict, then the packet 1300 is to be discarded or re-requested. If MACs 1320 are calculated and appended onto each packet 1315 according to the present invention, MACs 1320 may be used in place of the packet-wise CRC in telemetry systems of the prior art. To the extent that certain packets will be sent unsecured, as detailed variously herein, in additional an unkeyed integrity-check mechanism (like a CRC) may be applied. This integrity check could be realized through the use of a hardware CRC or alternatively, by using CBC-MAC with a publicly-known key and nonce (e.g., by using 0x00000000000000000000000000000000 for both).

While in this embodiment using a MAC 1320, the length of packet payloads 1315 (i.e. the portion of the packet which is to be encrypted) is 30 bytes, (thus requiring a nonce register block-number field 1235 of only 1 bit, the nonce register block-number field 1235 may be fixed at seven bits to provision for future telemetry schemes which might permit the use of longer packet payloads as long as 4096 bytes using the same nonce register structure 1110.

Figure 14:
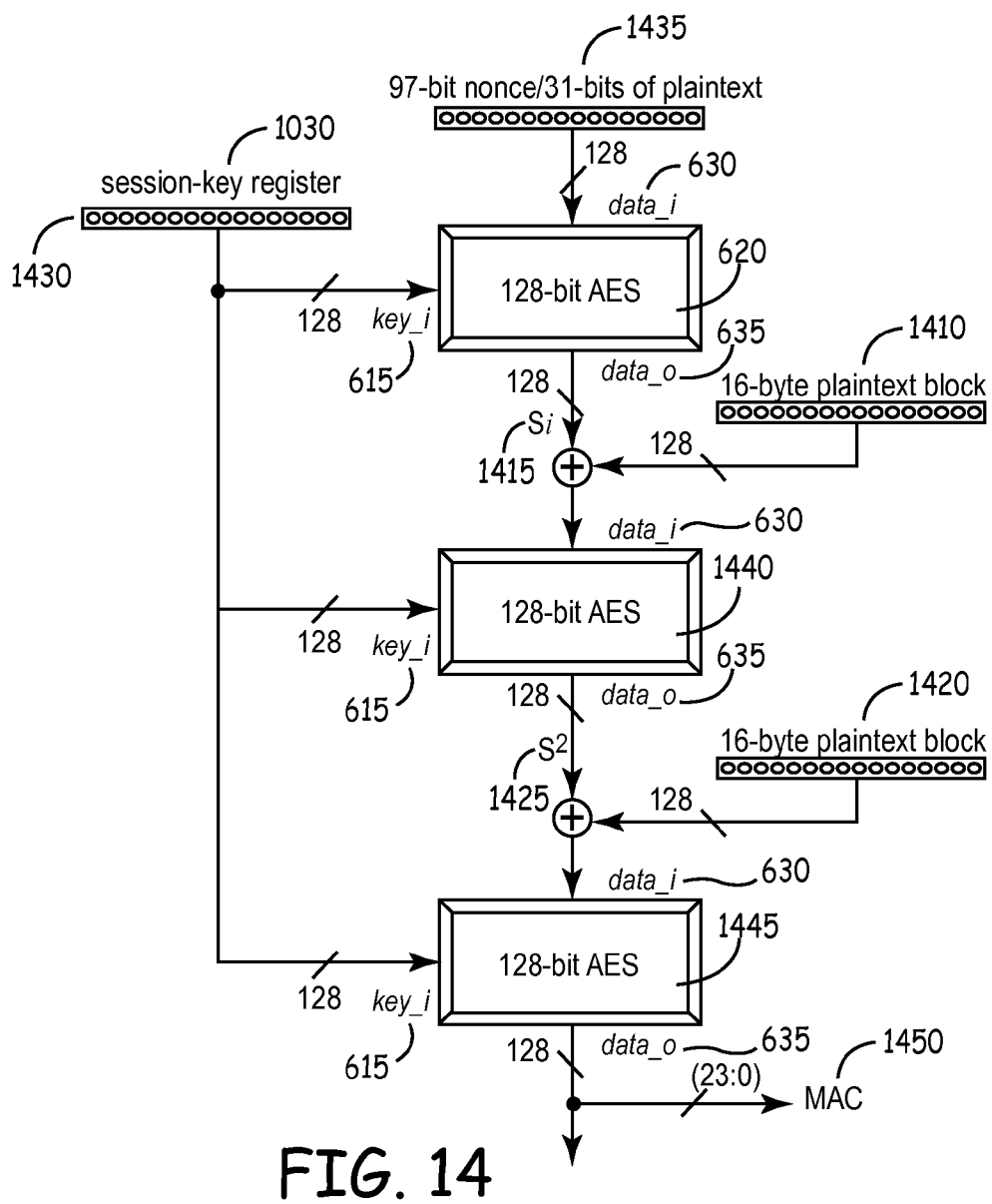
FIG. 14 shows the data flow for encryption/decryption and authentication of messages according to an embodiment of the present invention.

In a CBC-MAC generation/verification algorithm according to a representative embodiment of the present invention depicted in FIG. 14, initially, the shared session-key 1030 (the same one used for CTR-mode encryption/decryption) is loaded into the key_i input 615 of the block cipher 620 by way of a 128-bit register 1430. The data_i input 615 of the block cipher 620 may be loaded with a concatenation 1435 of the 97 most-significant bits of the nonce (truncating the block-number field as necessary) and up to the first 31 bits of the plaintext packet (typically consisting of header information). The mode bit 1230 of the nonce-register 1110 may be set to logical one. In a typical embodiment, regardless of whether the CBC-MAC algorithm is being used for MAC generation or MAC verification, CBC-MAC processing is to be done on the decrypted form (i.e., message plaintext) of each packet. In this embodiment, accordingly the received packets must be decrypted before their MAC can be verified.

The output (data_o) 635 of the first block-cipher 620 in FIG. 14 may be bitwise XORed to the next 128-bits following the plaintext concatenated to the 97 bit nonce at 1435. The result of this XOR is then loaded into input 630 of the second block-cipher 1440. The output 635 of the second block-cipher 1440 is then XORed with the last 128-bits of packet plaintext from 1315 of packet 1300 (zero padded as necessary), and then processed by the third block-cipher 1445. In this embodiment, as the bit sum of a packet header and packet payload is ≦287 bits, no further rounds of CBC-MAC are required as the MAC is the 128-bit output (data_o) of the third block. In the event that a MAC were needed on longer packets according to an alternative embodiment of the present invention, additional plaintext blocks could be processed by XOR-ing and passing the output through additional block ciphers 620. Generally, for m blocks of plaintext, m XOR/block-cipher rounds 630 would be required, where the data_o output 635 of the last block cipher would be the MAC 1450. Note that while three block-cipher cores 620, 1440, 1445 are depicted in FIG. 14, in certain embodiments only one core will actually be implemented in hardware; in practice, the XOR output will be routed to data_i input 630 of the first block cipher 620. The three cores 620, 1440, 1445 shown in FIG. 14 are meant only to illustrate the CBC-MAC algorithm.

As depicted in FIG. 14, in certain embodiments of the present invention, only the least-significant 24 bits (bits 23 through 0) of the CBC-MAC output 1450 will be appended onto the end of the processed packet 1300 as MAC 1320, which does not compromise the underlying cryptographic strength of the CBC-MAC function (e.g., 128-bits, as in this case).

Each device participating in a secured session will preferably increment its respective session nonce counter 1210 on the transmission and reception of every packet 1300. In this manner, because only one device in a secure-session is transmitting at a time, the nonce increment acts as a proxy token, thus ensuring that multiple devices cannot transmit simultaneously. Because in certain embodiments, telemetry packets are relatively long, nodes could conceivably lose nonce synchronization amongst a BAN group in certain circumstance. Where supported by the underlying communications protocol, in certain embodiments of the instant invention, the devices may periodically include their current plaintext nonces in frame headers to provide a nonce-synchronization check. In typical embodiments, nonce synchronization may generally be recovered by always including the current nonce 1110 in NACK packets, or through whatever native recovery techniques that exist in the underlying communications protocol. Preferably, all devices adhere to the rules that a) the counter within their copy of the session nonce should be at least as large as any nonce they that receive in a maintenance message and b) a new session key must be calculated when the nonce counter reaches 0xhFFFFFFFFFFFFFFFF, no nonce will be used twice, thus assuring message freshness, as described further herein.

Figure 15:
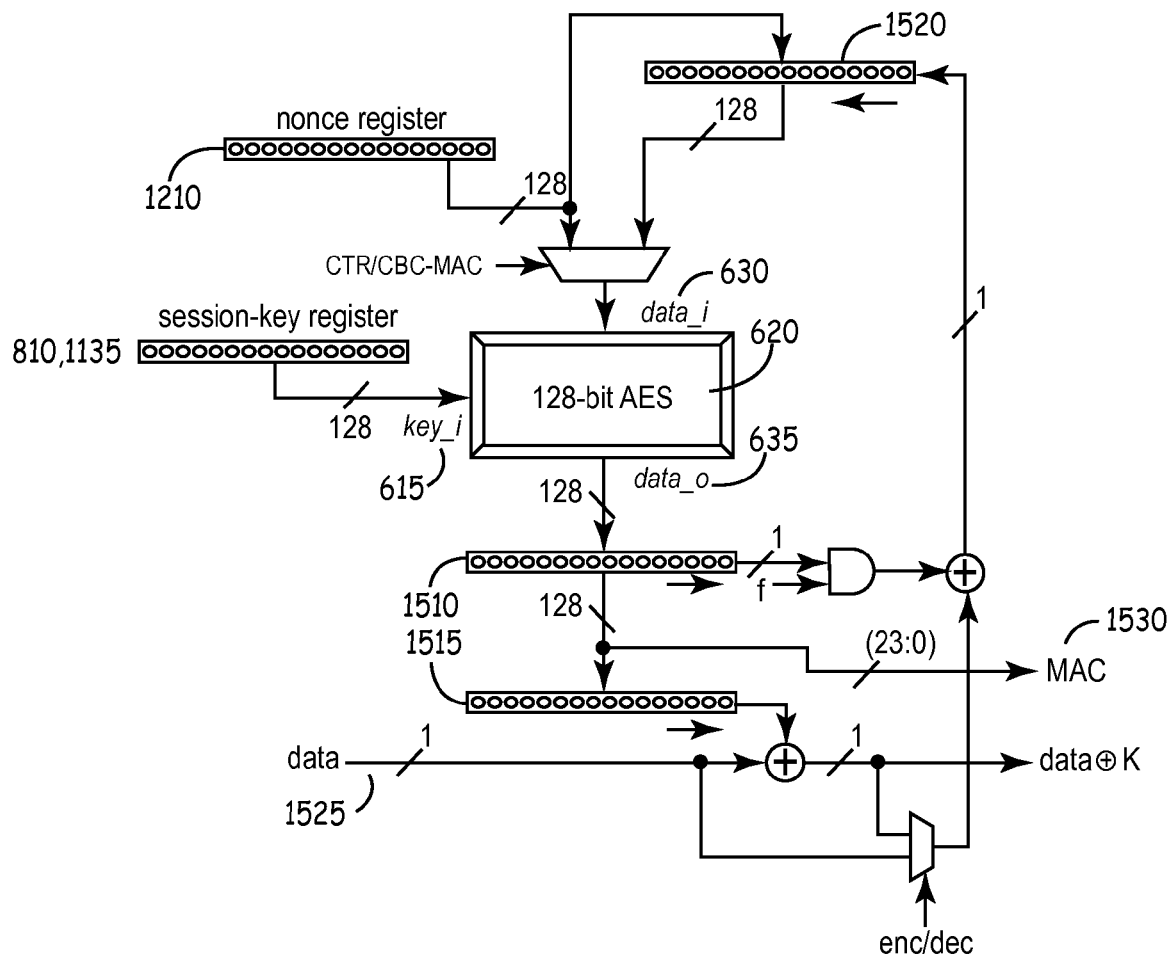
FIG. 15 depicts a schematic hardware architecture according to an embodiment of the present invention.

Preferably, encryption/decryption should be applied to telemetry packet payloads 1315, rather than headers 1310. This embodiment of the invention tends to minimize both the known-plaintext available to an attacker, as well as the length of the required keystream. Furthermore, this gives the block-cipher time to compute and buffer keystream material while the packet headers 1310 are propagating through the physical-layer hardware. While in certain embodiments of the present invention, a single block-cipher core 620 (e.g., AES block cipher) will be used to implement both ciphering and MAC functions, this preferably will be effected by first generating and storing enough keystream material, using CRT mode, for an entire packet's worth of payload data 1315, rather than alternating CTR mode with CBC-MAC mode per block at runtime. Once encrypted/decrypted 128-bit blocks are available, the CBC-MAC mode will be used successively to generate/verify the MAC. FIG. 15 illustrates a proposed hardware layout for the AES-based mixed use of CTR and CBC-MAC modes for packets according to an embodiment of the present invention (≦32-byte payload).

Generally, a hardware implementation of a node according to the current invention requires one instance of the 128-bit AES block cipher (and corresponding dedicated 128-bit registers) and keep-alive or non-volatile storage for the 128-bit BAN key. Because the session nonce consists solely of the instigating device's random-number contribution to the session key (Rx), all devices in a secured network know the session nonce without the need for any additional transmissions. As shown in FIG. 15, single block cipher 620 is used to process either keystream (via input 1510) or CBC-MAC input (via input 1515) to data_i input 630. The output 635 of block cipher 620, register 1515, is XORed with plaintext 1525 to encrypt plaintext data 1525.

In certain embodiments of the invention, an unkeyed integrity check will still be used to the extent that packets will need to be communicated unsecured (like the packets which are used to open a session and share random numbers). This integrity check may be implemented through, for example, the use of a hardware CRC or perhaps by using CBC-MAC with a publicly-known secret key and nonce (like 0x000000000000000000000000000000000 for both).

Keystream material is generated and stored in first and second keystream registers, 1510 and 1515, respectively. Once the keystream material in the second keystream 1515 register is used up, first keystream register 1510 parallel loads into the keystream register 1515. The first plaintext block is stored in the register 1520, and the resulting first MAC block following block-cipher processing 620, is stored in the first keystream register 1510 (once its keystream material is emptied into second keystream register 1515). The first MAC block is XORed with the second block of plaintext from 1525 and put through the block cipher 620. The least-significant 24 bits of the final MAC 1530 is then appended to the encrypted data 1315 of FIG. 13.

In a wireless telemetry system according to the present invention, typically communications sessions between in-vivo and in-vitro devices can be initiated, executed, and closed entirely wirelessly, as disclosed herein. Therefore, it is important to prevent unauthorized and/or malicious parties to communicate with implanted devices or other nodes of the BAN, as discussed. However, it will be appreciated that there may arise situations in practice where unauthorized in-vitro devices (such as physician programmer appliances, emergency-response equipment) and their users (unauthorized in the sense that they do not have access to an implant's secret key, but having a patient's express or implied consent or direction to access the patient's BAN) still need to communicate with an implanted device. Such situations may arise, for example, in emergency situations where a patient is undergoing a critical, and even life-threatening physiological event, whether or not caused by the implant itself. For example, the patient may conceivably be unconscious and without identification materials. Situations may also arise where full authentication, according to aspects of the invention as described above, is not feasible due to excessive inconvenience where authentication according to the protocols above is prohibitive or infeasible. For example, a patient may have traveled a great distance to a physician appointment, but upon arrival, found that he or she has forgotten or mislaid his or her smartcard, or other materials necessary to permit an in-vitro node to communicate with the implant, or the patient may have forgotten his or her authenticating password. In these situations, a "backdoor," i.e. a method of interfacing with an IMD BAN node (but, in representative embodiments, without any way to derive the node's secret device key $K_{dev}$), may permit legitimate access to the node in a manner that circumvents, on a limited basis, the security protocols of a system according to the invention; thus avoiding the inconvenience of rescheduling a patient's appointment, or in true emergency situations, enabling critical care to a patient.

In one embodiment of the invention, a convenient backdoor mechanism may be provided that would operate wirelessly, for example, over some distance, for example, as a wireless protocol. In certain embodiments of the instant invention, however, the backdoor would not be wireless, and equipment able to open the backdoor may be widely available (and accordingly, would be easy for an attacker to acquire). Accordingly, the backdoor in certain embodiments would not be implemented in a manner such that the security of all node devices sharing the key would be irrevocably compromised upon the acquisition of a node device by an attacker who is motivated for whatever reason to compromise the relative secrecy of the backdoor key. Therefore, in certain embodiments of the present invention in which a wireless backdoor is implemented, preferably only a limited amount of functionality of the entire implant or node (e.g., Alice 115) is operable upon communication of the backdoor key. For example, in certain implementations in which a wireless backdoor is available, wireless backdoors may be used solely to put implants in their respective quiescent (i.e., "stand-by") modes. More specifically, a pacemaker, for example, may go into a 60 bpm mode, while an implantable cardioverter defibrillator or neural stimulator or drug pump could be put into a therapy-suspension mode by means of the wireless backdoor.

Figure 16:
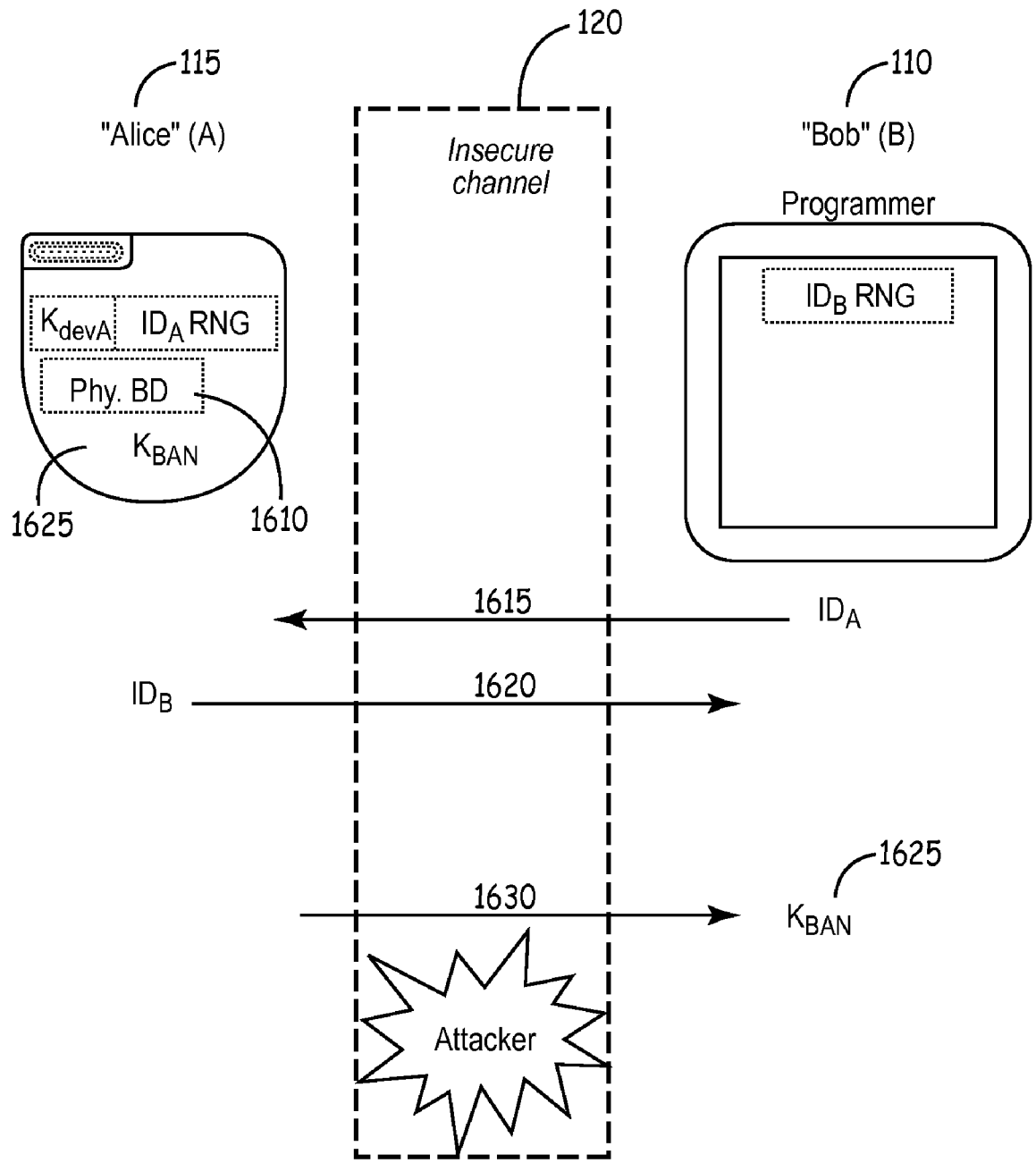
FIG. 16 depicts a network topography for an emergency access protocol of an embodiment of the present invention.

Referring to FIG. 16, in certain embodiments of the instant invention, a "physical" backdoor 1610, i.e., a method of access not using a wireless communications channel 120, is provided. In these embodiments, access to the BAN node 115 without authentication is effected only by physical contact (or close proximity) between the device seeking backdoor access 110, and the node to be accessed 115 and/or its patient (in the case of an implanted device). This may be implemented by the use of a near-field magnetic sensor, such as a Hall-effect sensor or magnetic reed switch, in certain BAN nodes 115. Preferably, this sensor 1610 does not effect a communications channel per se, but rather is used solely to put the module in an open mode where equipment can communicate with the implant(s) or other node, without the authentication requirements called for by embodiments of the invention (as described above). Alternatively, the backdoor may initiate means of near-range telemetry such as magnetic telemetry, in which the proximity actually enables use of a communication channel.

Also in certain embodiments, once the emergency equipment 110 closes the communications session, the backdoor 1610 would close, i.e., the open communications channel would be closed down, and further communications to the device 115 would require the applicable authentication information, for example as provided herein, or alternately the establishment of another backdoor communications session. The effect of the use of this backdoor may be compared to the recessed reset button of a wireless network appliance, such as a wireless router. While the reset may allow aspects of the wireless router to be changed by a remote third party, the state is not provided without a physical action at the device. This physical access to the device is taken as a proxy for administrative authorization to administer changes to the device or node.

The backdoor may also be used as a preferred means of extracting $K_{BAN}$ from an IMD for the purposes of delivering that $K_{BAN}$ to other devices in the BAN. The backdoor may also be used to request that an IMD transmit an ephemeral $K_{BAN}$ (a locally generated random number to be temporarily used as the $K_{BAN}$) which is only valid for the duration of that telemetry session. In implementations where backdoor access can result in the wireless transmission of $K_{BAN}$ or an ephemeral $K_{BAN}$, it may be the case that added credentials are required in order for the IDM to transmit the $K_{BAN}$, with respect to those credentials needed to recover an ephemeral $K_{BAN}$. Such credentials may include activation of a proximity switch for an extended period of time, e.g., 10 seconds, where recovery of an ephemeral $K_{BAN}$ might be authorized on activation of the same proximity switch for only three seconds.

The backdoor 1610 to the IMD 115 may be embodied as follows: Initially, Alice 115 and Bob 110 open a communications session over insecure channel 120 by exchanging IDs (ID$_A$, ID$_B$) via messages 1615 and 1620. Bob 110 then, via insecure channel 120, asks Alice 115 to power-up her backdoor circuitry 1610, that otherwise would be turned off and would not respond to any external event such as the proximity of a magnet, for example—when off, the backdoor may be said to be "locked." Once the backdoor circuitry 1610 is on, thus "unlocking" the backdoor 1610, Bob 110 may physically open Alice's backdoor by means such as a magnetic switch or Hall-effect sensor, as described above. Preferably, if the backdoor 1610 is not physically opened before a pre-defined time-out, Alice 115 will automatically power down her backdoor circuitry 1610, relocking the backdoor 1610 to avoid attacks where proximity to the host patient is available to the attacker.

Following the opening of the backdoor 1610, Alice 115 will reduce her RF transmission power (thereby reducing the effective transmission range of the signal) and then send Bob 110 K$_{BAN}$ 1625 by via message 1630, whereupon Alice 115 promptly powers down her backdoor circuitry 1610. In representative embodiments, no request by Bob 110 for the BAN key is necessary, as the request for the BAN key is implicit in the initiation of the backdoor protocol.

Figure 17:
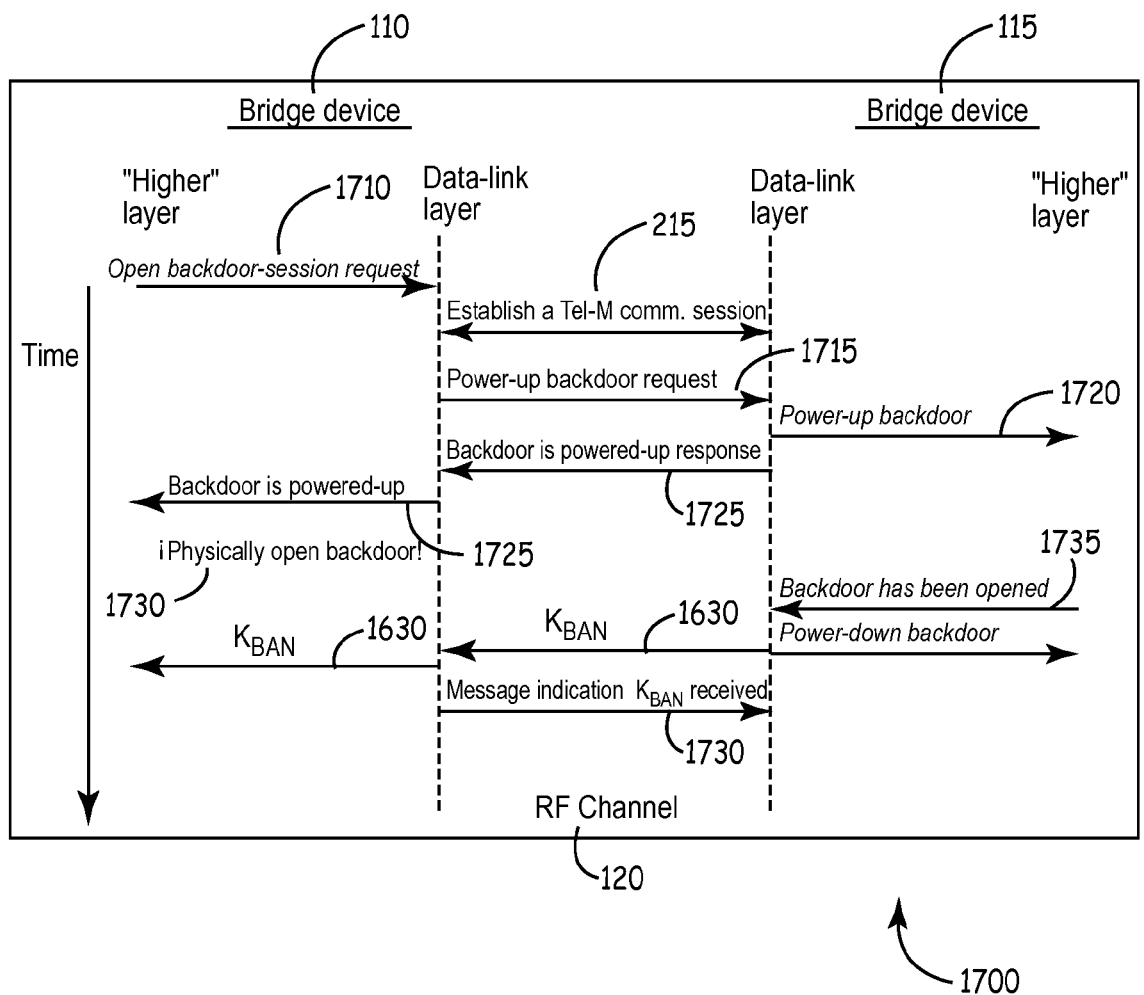
FIG. 17 depicts a pseudo-protocol and data flow for an emergency access protocol according to an embodiment of the present invention.

FIG. 17 depicts a pseudo-protocol and data flow for an emergency access protocol according to the embodiment of FIG. 16. As indicated in FIG. 17, a bridge device 110 can obtain a BAN key by means of a backdoor session request 1710. Following the backdoor session request 1710, the two nodes establish an unsecured telemetry session at 215. Bridge device 110 may then request 1715 that backdoor circuitry 1610 be powered up. In response, IMD 115 powers up its backdoor circuitry 1610 at 1720, and at 1725 confirms to bridge device 110 that backdoor circuitry 1610 is powered up. Bridge device 110 may then activate the powered-up backdoor 1610 by means of proximity to the magnetic switch, Hall-effect sensor, or other proximity-based switch comprising the backdoor 1610; indicated by 1730.

Upon the opening 1730 of the backdoor 1610, IMD 115 realizes that the backdoor has been opened by the proximate node 110 as indicated at 1735, and subsequently transmits at 1625 the BAN key over the insecure telemetry channel 120. In certain embodiments, bridge device 110 may transmit confirmation of the receipt of the BAN key at 1730, however in typical embodiments the IMD 115 promptly powers down backdoor 1610 upon sending of the BAN key, and another request 1715 for the opening of the backdoor will be required.

The invention claimed is:

1. In a telecommunications network having at least first and second nodes in communication with each other, a method of making secure at least one communication between the at least first and second nodes during a communication session, comprising the steps of:

assigning to each node an identifier unique to each node within the network;

assigning to each node a device key unique to each node within the network;

assigning to the network a network key;

establishing a communication session between the at least first and second nodes;

providing the network key to at least the second node;

providing the second node's identifier to the first node;

providing to the first node the second node's device key in a manner not subject to unauthorized discovery;

preparing a first communication comprising the first node's identifier and the second node's identifier;

securing the first communication with the second node's device key;

transmitting the first communication to the second node;

decrypting at the second node the first communication using the second node's device key;

providing the first node with the network key subject to verification that the second node's device key was used to secure the first communication; and securing a second communication among the at least first and second nodes using the network key.

2. The method of making secure the at least one communication between the at least first and second nodes during a communication session of claim 1, wherein the provision to the first node of the second node's device key in a manner not subject to unauthorized discovery is effected by entry of the device key from a physical token.

3. The method of making secure the at least one communication between the at least first and second nodes during a communication session of claim 1, wherein the step of providing to the first node the second node's device key in a manner not subject to unauthorized discovery comprises the steps of:

placing the second node's device key on a physical token; and transferring the second node's device key from the physical token to the first node.

4. The method of making secure the at least one communication between the at least first and second nodes during a communication session of claim 3, wherein in the step of providing to the first node the second node's device key in a manner not subject to unauthorized discovery, the second node's device key is stored on the physical token and the step of transferring of the second node's device key from the physical token to the first node is done electronically.

5. The method of making secure the at least one communication between the at least first and second nodes during a communication session of claim 4, wherein the step of transferring of the second node's device key from the physical token to the first node electronically is done in a manner in which the first node is provided the device key in encrypted form.

6. The method of making secure the at least one communication between the at least first and second nodes during a communication session of claim 3, wherein the physical token is a key fob containing at least one processor.

7. The method of making secure the at least one communication between the at least first and second nodes during a communication session of claim 6, wherein the step of securing the first communication is effected by means of the at least one processor of the key fob.

8. The method of making secure the at least one communication between the at least first and second nodes during a communication session of claim 3, wherein the physical token is a smartcard.

9. The method of making secure the at least one communication between the at least first and second nodes during a communication session of claim 8, wherein the step of securing the first communication is effected by the smartcard.

10. The method of making secure the at least one communication between the at least first and second nodes during a communication session of claim 9, wherein the second node's device key is encrypted by authentication information and stored on the smartcard.

11. The method of making secure the at least one communication between the at least first and second nodes during a communication session of claim 10, where the authentication information comprises a string of password characters.

12. The method of making secure the at least one communication between the at least first and second nodes during a communication session of claim 10, wherein the authentication information comprises biometric parameters.

13. The method of making secure the at least one communication between the at least first and second nodes during a communication session of claim 1, wherein the network includes a medical data service network.

14. The method of making secure the at least one communication between the at least first and second nodes during a communication session of claim 1, wherein at least one of the at least first and second nodes comprises an implantable medical device.

15. In a telecommunications network having at least first and second nodes in communication with each other, a method of making secure at least one communication between the at least first and second nodes during a communication session, comprising the steps of:
assigning to each node an identifier unique to each node within the network;
assigning to each node a device key unique to each node within the network;
assigning to the network a network key;
establishing a communication session between the at least first and second nodes;
providing the network key to at least the first node;
providing the second node's identifier to the first node;
securely providing to the first node the second node's device key;
transmitting from the second node to the first node a first communication comprising the first node's identifier, the second node's identifier, and the network key, wherein the first communication is secured with the second node's device key; and
securing a second communication among the at least first and second nodes using the network key.

16. The method of making secure the at least one communication between the at least first and second nodes during a communication session of claim 15, wherein the step of securing the second communication among the at least first and second nodes using the network key comprises the steps of:
generating a session key at the first node as a function of the network key and a first arbitrary number;
independently generating the session key at the second node as a function of the network key and the first arbitrary number; and
using the session key to secure the second communication among the at least first and second nodes.

17. The method of making secure the at least one communication between the at least first and second nodes during a communication session of claim 16, wherein the first arbitrary number is a pseudorandom number.

18. The method of making secure at least one communication between the at least first and second nodes during a communication session of claim 16, wherein the first arbitrary number is generated by a method of arbitrary number generation, comprising the steps of:
generating a second arbitrary number at the first node;
providing the second arbitrary number to the second node;
generating a third arbitrary number at the second node;
providing the third arbitrary number to the first node; and
generating the first arbitrary number as a function of both the second arbitrary number and the third arbitrary number.

19. The method of making secure the at least one communication between the at least first and second nodes during a communication session of claim 18, wherein at least one of the second arbitrary number and third arbitrary number is a pseudorandom number.

20. The method of making secure the at least one communication between the at least first and second nodes during a communication session of claim 16, wherein the step of securing the second communication among the at least first and second nodes with the session key comprises the step of executing bitwise modulo-2 addition between the output of a cipher and a message comprising plaintext, wherein the output of the cipher is a function of both the session key and a first nonce that is unique within the communication session.

21. The method of making secure the at least one communication between the at least first and second nodes during a communication session of claim 20, wherein the first nonce is a function of the number of discrete communications that have been transmitted between the at least first and second nodes during the communication session, and a size of the discrete communications.

22. The method of making secure the at least one communication between the at least first and second nodes during a communication session of claim 21, wherein the discrete communications are packets.

23. The method of making secure the at least one communication between the at least first and second nodes during a communication session of claim 22, wherein the size of the discrete communications is measured in blocks.

24. The method of making secure the at least one communication between the at least first and second nodes during a communication session of claim 23, wherein the cipher is a block cipher.

25. The method of making secure the at least one communication between the at least first and second nodes during a communication session of claim 24, further comprising the step of appending to each discrete communication an authentication tag derived from the discrete communication to which it is appended.

26. The method of making secure the at least one communication between the at least first and second nodes during a communication session of claim 25, wherein the authentication tag is a function of the session key and the plaintext of the message being communicated.

27. The method of making secure the at least one communication between the at least first and second nodes during a communication session of claim 26, wherein the authentication tag is also a function of a second nonce, wherein the second nonce is a function of the number of discrete communications that have been transmitted between the at least first and second nodes of the network during the communication session.

28. The method of making secure the at least one communication between the at least first and second nodes during a communication session of claim 25, wherein the authentication tag is a function of the session key, the plaintext of the message being communicated, and the number of discrete communications that have been transmitted between the at least first and second nodes of the network during the communication session.

29. The method of making secure the at least one communication between the at least first and second nodes during a communication session of claim 25, wherein the authentication tag is the result of a hash function performed on the discrete communication to which the authentication tag is appended.

* * * * *